(12) United States Patent
Lee et al.

(10) Patent No.: US 11,596,451 B2
(45) Date of Patent: Mar. 7, 2023

(54) IMPLANT CONNECTORS AND RELATED METHODS

(71) Applicant: Medos International Sarl, Le Locle (CH)

(72) Inventors: Kevin Lee, Canton, MA (US); Christopher Ramsay, West Wareham, MA (US); J. Riley Hawkins, Cumberland, RI (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 488 days.

(21) Appl. No.: 16/688,578

(22) Filed: Nov. 19, 2019

(65) Prior Publication Data
US 2020/0085473 A1 Mar. 19, 2020

Related U.S. Application Data

(63) Continuation of application No. 15/158,127, filed on May 18, 2016, now Pat. No. 10,517,647.

(51) Int. Cl.
*A61B 17/70* (2006.01)
*A61B 17/88* (2006.01)

(52) U.S. Cl.
CPC ................................ *A61B 17/7049* (2013.01)

(58) Field of Classification Search
CPC .............. A61B 17/7049; A61B 17/705; A61B 17/7052
USPC ......................... 606/250, 252, 260, 278, 279
See application file for complete search history.

(56) References Cited

U.S. PATENT DOCUMENTS

| | | | |
|---|---|---|---|
| 5,261,909 A | 11/1993 | Sutterlin et al. |
| 5,312,405 A | 5/1994 | Korotko et al. |
| 5,569,246 A | 10/1996 | Ojima et al. |
| 5,613,968 A | 3/1997 | Lin |
| 5,667,506 A | 9/1997 | Sutterlin |
| 5,669,910 A | 9/1997 | Korhonen et al. |
| 5,709,685 A | 1/1998 | Dombrowski et al. |
| 5,716,355 A | 2/1998 | Jackson et al. |
| 5,725,528 A | 3/1998 | Errico et al. |
| 5,769,857 A | 6/1998 | Reztzov et al. |
| 5,776,135 A | 7/1998 | Errico et al. |

(Continued)

FOREIGN PATENT DOCUMENTS

| | | |
|---|---|---|
| CN | 101198284 A | 6/2008 |
| CN | 201194833 Y | 2/2009 |

(Continued)

OTHER PUBLICATIONS

U.S. Appl. No. 15/158,127, filed May 18, 2016, Implant Connectors and Related Methods.

(Continued)

*Primary Examiner* — Eduardo C Robert
*Assistant Examiner* — David C Comstock
(74) *Attorney, Agent, or Firm* — Barnes & Thornburg LLP

(57) ABSTRACT

Implant connectors and related methods are disclosed herein. In some embodiments, a connector can include a low-profile portion to facilitate use of the connector in surgical applications where space is limited. In some embodiments, a connector can include a biased rod-pusher to allow the connector to "snap" onto a rod and/or to "drag" against the rod, e.g., for provisional positioning of the connector prior to locking.

24 Claims, 17 Drawing Sheets

(56) References Cited

U.S. PATENT DOCUMENTS

| | | |
|---|---|---|
| 5,876,403 A | 3/1999 | Shitoto |
| 5,885,284 A | 3/1999 | Errico et al. |
| 5,980,523 A | 11/1999 | Jackson |
| 6,050,997 A | 4/2000 | Mullane |
| 6,083,226 A | 7/2000 | Fiz |
| 6,096,039 A | 8/2000 | Stoltenberg et al. |
| 6,231,575 B1 | 5/2001 | Krag |
| 6,238,396 B1 | 5/2001 | Lombardo |
| 6,248,104 B1 | 6/2001 | Chopin et al. |
| 6,280,443 B1 | 8/2001 | Gu et al. |
| 6,309,390 B1 | 10/2001 | Le Couedic et al. |
| 6,328,739 B1 | 12/2001 | Liu et al. |
| 6,328,740 B1 | 12/2001 | Richelsoph |
| 6,402,751 B1 | 6/2002 | Hoeck et al. |
| 6,468,276 B1 | 10/2002 | McKay |
| 6,478,798 B1 | 11/2002 | Howland |
| 6,524,310 B1 | 2/2003 | Lombardo et al. |
| 6,551,318 B1 | 4/2003 | Stahurski |
| 6,554,832 B2 | 4/2003 | Shluzas |
| 6,592,585 B2 | 7/2003 | Lee et al. |
| 6,616,668 B2 | 9/2003 | Altarac et al. |
| 6,676,661 B1 | 1/2004 | Martin Benlloch et al. |
| 6,736,775 B2 | 5/2004 | Phillips |
| 6,736,820 B2 | 5/2004 | Biedermann et al. |
| 6,783,526 B1 | 8/2004 | Lin et al. |
| 6,786,907 B2 | 9/2004 | Lange |
| 6,793,657 B2 | 9/2004 | Lee et al. |
| 6,974,460 B2 | 12/2005 | Carbone et al. |
| 7,029,474 B2 | 4/2006 | Richelsoph et al. |
| 7,104,993 B2 | 9/2006 | Baynham et al. |
| 7,122,036 B2 | 10/2006 | Vanacker |
| 7,163,538 B2 | 1/2007 | Altarac et al. |
| 7,166,108 B2 | 1/2007 | Mazda et al. |
| 7,179,261 B2 | 2/2007 | Sicvol et al. |
| 7,189,236 B2 | 3/2007 | Taylor et al. |
| 7,485,132 B1 | 2/2009 | McBride et al. |
| 7,572,277 B2 | 8/2009 | Roussouly et al. |
| 7,575,587 B2 | 8/2009 | Rezach et al. |
| 7,585,314 B2 | 9/2009 | Taylor et al. |
| 7,628,799 B2 | 12/2009 | Richelsoph et al. |
| 7,666,210 B2 | 2/2010 | Franck et al. |
| 7,704,270 B2 | 4/2010 | De Coninck |
| 7,717,938 B2 | 5/2010 | Kim et al. |
| 7,717,940 B2 | 5/2010 | Woods et al. |
| 7,744,632 B2 | 6/2010 | Usher |
| 7,744,634 B2 | 6/2010 | Farris |
| 7,753,940 B2 | 7/2010 | Veldman et al. |
| 7,771,474 B2 | 8/2010 | Cordaro |
| 7,789,897 B2 | 9/2010 | Sanders |
| 7,794,478 B2 | 9/2010 | Nilsson |
| 7,803,174 B2 | 9/2010 | Denis et al. |
| 7,806,912 B2 | 10/2010 | Lawton et al. |
| 7,833,248 B2 | 11/2010 | Markworth et al. |
| 7,837,714 B2 | 11/2010 | Drewry et al. |
| 7,842,071 B2 | 11/2010 | Hawkes |
| 7,901,434 B2 | 3/2011 | Drewry et al. |
| 7,909,854 B2 | 3/2011 | Schwab |
| 7,922,746 B2 | 4/2011 | Miller |
| 7,922,747 B2 | 4/2011 | Kirschman |
| 7,927,355 B2 | 4/2011 | Berrevoets et al. |
| 7,942,901 B2 | 5/2011 | Rezach |
| 7,947,066 B2 | 5/2011 | Tepper et al. |
| 7,959,653 B2 | 6/2011 | Thramann et al. |
| 7,993,371 B2 | 8/2011 | Farris |
| 8,016,862 B2 | 9/2011 | Felix et al. |
| 8,025,679 B2 | 9/2011 | Nichols et al. |
| 8,062,338 B2 | 11/2011 | McBride et al. |
| 8,075,594 B2 | 12/2011 | Purcell |
| 8,080,037 B2 | 12/2011 | Butler et al. |
| 8,097,022 B2 | 1/2012 | Marik |
| 8,109,974 B2 | 2/2012 | Boomer et al. |
| 8,114,133 B2 | 2/2012 | Logan |
| 8,147,519 B2 | 4/2012 | Wilcox |
| 8,152,851 B2 | 4/2012 | Mueller et al. |
| 8,167,908 B2 | 5/2012 | Ely et al. |
| 8,172,879 B2 | 5/2012 | Butler et al. |
| 8,192,467 B2 | 6/2012 | Felix et al. |
| 8,197,515 B2 | 6/2012 | Levy et al. |
| 8,236,028 B2 | 8/2012 | Kalfas et al. |
| 8,241,334 B2 | 8/2012 | Butler et al. |
| 8,246,657 B1 | 8/2012 | Samuel |
| 8,246,665 B2 | 8/2012 | Butler et al. |
| 8,262,700 B2 | 9/2012 | Cho et al. |
| 8,262,701 B2 | 9/2012 | Rathbun et al. |
| 8,292,924 B2 | 10/2012 | Neary et al. |
| 8,298,266 B2 | 10/2012 | Miller |
| 8,298,269 B2 | 10/2012 | Null et al. |
| 8,317,837 B2 | 11/2012 | Rezach et al. |
| 8,337,527 B2 | 12/2012 | Hawkins et al. |
| 8,337,532 B1 | 12/2012 | McLean et al. |
| 8,366,749 B2 | 2/2013 | Sweeney |
| 8,366,750 B2 | 2/2013 | Iott et al. |
| 8,414,616 B2 | 4/2013 | Berrevoets et al. |
| 8,414,617 B2 | 4/2013 | Young et al. |
| 8,419,771 B2 | 4/2013 | Poirier et al. |
| 8,419,773 B2 | 4/2013 | Biedermann et al. |
| 8,430,916 B1 | 4/2013 | Winslow et al. |
| 8,460,342 B2 | 6/2013 | Courtney et al. |
| 8,470,001 B2 | 6/2013 | Trautwein et al. |
| 8,591,550 B2 | 11/2013 | Ludwig et al. |
| 8,617,213 B2 | 12/2013 | Moore et al. |
| 8,628,559 B2 | 1/2014 | Iott et al. |
| 8,641,739 B2 | 2/2014 | McLean et al. |
| 8,657,856 B2 | 2/2014 | Gephart et al. |
| 8,668,721 B2 | 3/2014 | Miller |
| 8,715,323 B2 | 5/2014 | Ballard et al. |
| 8,721,689 B2 | 5/2014 | Butler et al. |
| 8,728,124 B2 | 5/2014 | Miller |
| 8,758,411 B1 | 6/2014 | Rayon et al. |
| 8,771,319 B2 | 7/2014 | Prajapati |
| 8,808,332 B2 | 8/2014 | Iott et al. |
| 8,828,056 B2 | 9/2014 | Buss et al. |
| 8,864,798 B2 | 10/2014 | Weiman et al. |
| 8,864,799 B2 | 10/2014 | Kraus |
| 8,870,923 B2 | 10/2014 | Richelsoph |
| 8,882,803 B2 | 11/2014 | Iott et al. |
| 8,888,777 B2 | 11/2014 | Mullaney |
| 8,888,819 B2 | 11/2014 | Frasier et al. |
| 8,920,471 B2 | 12/2014 | Barrus et al. |
| 8,920,475 B1 | 12/2014 | Ziemek et al. |
| 8,945,186 B2 | 2/2015 | Walker et al. |
| 8,951,289 B2 | 2/2015 | Matityahu |
| 8,998,956 B2 | 4/2015 | George et al. |
| 8,998,961 B1 | 4/2015 | Ziemek et al. |
| 9,005,249 B2 | 4/2015 | Rinner et al. |
| 9,023,087 B2 | 5/2015 | Frankel et al. |
| 9,055,980 B2 | 6/2015 | Biedermann |
| 9,060,815 B1 | 6/2015 | Gustine et al. |
| 9,072,547 B2 | 7/2015 | Harper et al. |
| 9,084,630 B2 | 7/2015 | Mullaney |
| 9,095,380 B2 | 8/2015 | Mir et al. |
| 9,101,400 B2 | 8/2015 | Trieu et al. |
| 9,101,405 B2 | 8/2015 | Dickinson et al. |
| 9,107,703 B2 | 8/2015 | Torres |
| 9,113,961 B2 | 8/2015 | Larroque-Lahitette |
| 9,119,675 B2 | 9/2015 | Lee et al. |
| 9,125,691 B2 | 9/2015 | Gunn |
| 9,131,963 B2 | 9/2015 | Predick |
| 9,131,964 B2 | 9/2015 | Blain et al. |
| 9,149,301 B2 | 10/2015 | Asaad et al. |
| 9,155,565 B2 | 10/2015 | Boomer et al. |
| 9,155,580 B2 | 10/2015 | Cormier et al. |
| 9,186,184 B2 | 11/2015 | Janowski |
| 9,198,696 B1 | 12/2015 | Bannigan et al. |
| 9,204,901 B2 | 12/2015 | Black et al. |
| 9,220,541 B1 | 12/2015 | Dant et al. |
| 9,247,964 B1 | 2/2016 | Shoshtaev |
| 9,265,548 B2 | 2/2016 | Jones et al. |
| 9,271,763 B2 | 3/2016 | Barrus et al. |
| 9,339,307 B2 | 5/2016 | McClintock et al. |
| 9,345,521 B2 | 5/2016 | Ziolo |
| 9,421,041 B2 | 8/2016 | Richelsoph |
| 9,433,445 B2 | 9/2016 | Ramsay et al. |
| 9,451,994 B1 | 9/2016 | Whipple et al. |

(56) References Cited

U.S. PATENT DOCUMENTS

| | | | |
|---|---|---|---|
| 9,474,554 B2 | 10/2016 | Strnad | |
| 9,517,089 B1 | 12/2016 | Casey et al. | |
| 9,561,058 B2 | 2/2017 | Lange et al. | |
| 9,579,126 B2 | 2/2017 | Zhang et al. | |
| 9,615,867 B2 | 4/2017 | Picetti et al. | |
| 9,629,663 B2 | 4/2017 | Ludwig et al. | |
| 9,649,136 B2 | 5/2017 | George et al. | |
| 9,693,808 B2 | 7/2017 | Fauth et al. | |
| 9,724,131 B2 | 8/2017 | Bootwala et al. | |
| 9,770,269 B1 | 9/2017 | Shoshtaev | |
| 9,956,009 B1 | 5/2018 | Shoshtaev | |
| 10,238,432 B2 | 3/2019 | Carruth et al. | |
| 10,321,939 B2 | 6/2019 | Lee et al. | |
| 10,398,476 B2 | 9/2019 | Lee et al. | |
| 10,492,835 B2 | 12/2019 | Lee et al. | |
| 10,517,647 B2 | 12/2019 | Lee et al. | |
| 10,561,454 B2 | 2/2020 | Lee et al. | |
| 10,966,761 B2 | 4/2021 | Lee et al. | |
| 11,058,463 B2 | 7/2021 | Lee et al. | |
| 11,076,890 B2 | 8/2021 | Ortiz et al. | |
| 11,160,583 B2 | 11/2021 | Lee et al. | |
| 11,382,676 B2 | 7/2022 | Lee et al. | |
| 2002/0032442 A1* | 3/2002 | Altarac | A61B 17/7052 606/252 |
| 2002/0042614 A1 | 4/2002 | Ueyama et al. | |
| 2003/0045878 A1 | 3/2003 | Petit et al. | |
| 2003/0045879 A1 | 3/2003 | Minfelde et al. | |
| 2003/0153914 A1 | 8/2003 | Oribe et al. | |
| 2004/0111088 A1 | 6/2004 | Picetti et al. | |
| 2004/0147929 A1 | 7/2004 | Biedermann et al. | |
| 2004/0162558 A1 | 8/2004 | Hegde et al. | |
| 2005/0131404 A1 | 6/2005 | Mazda et al. | |
| 2005/0149019 A1 | 7/2005 | Sasing et al. | |
| 2005/0171537 A1 | 8/2005 | Mazel et al. | |
| 2005/0228326 A1 | 10/2005 | Kalfas et al. | |
| 2005/0228377 A1 | 10/2005 | Chao et al. | |
| 2005/0228378 A1* | 10/2005 | Kalfas | A61B 17/7049 606/252 |
| 2005/0228382 A1 | 10/2005 | Richelsoph et al. | |
| 2006/0039750 A1 | 2/2006 | Thomke et al. | |
| 2006/0058789 A1 | 3/2006 | Kim et al. | |
| 2006/0064090 A1 | 3/2006 | Park | |
| 2006/0064091 A1 | 3/2006 | Ludwig et al. | |
| 2006/0079892 A1 | 4/2006 | Roychowdhury et al. | |
| 2006/0177263 A1 | 8/2006 | Thomke et al. | |
| 2006/0195096 A1 | 8/2006 | Lee et al. | |
| 2006/0206114 A1* | 9/2006 | Ensign | A61B 17/7034 606/279 |
| 2006/0229611 A1 | 10/2006 | Avery et al. | |
| 2006/0241598 A1 | 10/2006 | Khalili | |
| 2006/0282074 A1 | 12/2006 | Renaud et al. | |
| 2007/0049932 A1 | 3/2007 | Richelsoph et al. | |
| 2007/0100339 A1 | 5/2007 | Clement et al. | |
| 2007/0123860 A1* | 5/2007 | Francis | A61B 17/7035 606/250 |
| 2007/0173825 A1 | 7/2007 | Sharifi-Mehr et al. | |
| 2007/0173829 A1 | 7/2007 | Drewry et al. | |
| 2007/0233062 A1 | 10/2007 | Berry | |
| 2007/0233090 A1 | 10/2007 | Naifeh et al. | |
| 2007/0250061 A1 | 10/2007 | Chin et al. | |
| 2007/0270805 A1 | 11/2007 | Miller et al. | |
| 2007/0270817 A1 | 11/2007 | Rezach | |
| 2007/0270818 A1 | 11/2007 | Rezach | |
| 2007/0276384 A1 | 11/2007 | Spratt | |
| 2008/0021466 A1 | 1/2008 | Shadduck et al. | |
| 2008/0045963 A1 | 2/2008 | Abdou | |
| 2008/0058805 A1 | 3/2008 | Stuart | |
| 2008/0082112 A1 | 4/2008 | Lawton et al. | |
| 2008/0109039 A1 | 5/2008 | Michielli et al. | |
| 2008/0177318 A1 | 7/2008 | Veldman et al. | |
| 2008/0177323 A1 | 7/2008 | Null et al. | |
| 2008/0234743 A1 | 9/2008 | Marik | |
| 2008/0255617 A1 | 10/2008 | Cho et al. | |
| 2008/0262552 A1 | 10/2008 | Kim | |
| 2008/0262553 A1 | 10/2008 | Hawkins et al. | |
| 2008/0269810 A1 | 10/2008 | Zhang et al. | |
| 2008/0281361 A1 | 11/2008 | Vittur et al. | |
| 2009/0036929 A1 | 2/2009 | Reglos et al. | |
| 2009/0082812 A1 | 3/2009 | Lewis | |
| 2009/0105765 A1 | 4/2009 | Strnad | |
| 2009/0157120 A1 | 6/2009 | Marino et al. | |
| 2009/0163956 A1 | 6/2009 | Biedermann et al. | |
| 2009/0187217 A1 | 7/2009 | Weiman et al. | |
| 2009/0204153 A1 | 8/2009 | Suzuki et al. | |
| 2009/0222042 A1 | 9/2009 | Firkins et al. | |
| 2009/0228046 A1 | 9/2009 | Garamszegi | |
| 2009/0249851 A1 | 10/2009 | Isaacs | |
| 2010/0004686 A1 | 1/2010 | Lemoine | |
| 2010/0004693 A1 | 1/2010 | Miller et al. | |
| 2010/0010545 A1 | 1/2010 | Park et al. | |
| 2010/0087864 A1 | 4/2010 | Klein et al. | |
| 2010/0087867 A1 | 4/2010 | Klein et al. | |
| 2010/0094345 A1 | 4/2010 | Saidha et al. | |
| 2010/0094346 A1 | 4/2010 | Matityahu | |
| 2010/0094349 A1 | 4/2010 | Hammer et al. | |
| 2010/0114165 A1 | 5/2010 | Ely | |
| 2010/0114167 A1 | 5/2010 | Wilcox et al. | |
| 2010/0160981 A1 | 6/2010 | Butler et al. | |
| 2010/0204733 A1 | 8/2010 | Rathbun et al. | |
| 2010/0241171 A1 | 9/2010 | Clement et al. | |
| 2010/0274286 A1 | 10/2010 | Blain et al. | |
| 2010/0280552 A1 | 11/2010 | Lee | |
| 2010/0298884 A1 | 11/2010 | Faizan et al. | |
| 2010/0324599 A1 | 12/2010 | Montello et al. | |
| 2011/0034957 A1 | 2/2011 | Biedermann | |
| 2011/0046675 A1 | 2/2011 | Barrus et al. | |
| 2011/0066187 A1 | 3/2011 | Fang et al. | |
| 2011/0087287 A1 | 4/2011 | Reeder, Jr. et al. | |
| 2011/0087288 A1 | 4/2011 | Stevenson et al. | |
| 2011/0098748 A1 | 4/2011 | Jangra | |
| 2011/0106178 A1 | 5/2011 | Schwab | |
| 2011/0112533 A1 | 5/2011 | Venturini et al. | |
| 2011/0112580 A1 | 5/2011 | Clement et al. | |
| 2011/0137345 A1 | 6/2011 | Stoll et al. | |
| 2011/0152936 A1 | 6/2011 | Gil et al. | |
| 2011/0196425 A1 | 8/2011 | Rezach et al. | |
| 2011/0245872 A1 | 10/2011 | Nilsson | |
| 2011/0245878 A1 | 10/2011 | Franks et al. | |
| 2011/0307018 A1 | 12/2011 | Zucherman et al. | |
| 2012/0029571 A1 | 2/2012 | Schwab et al. | |
| 2012/0059421 A1 | 3/2012 | Aferzon | |
| 2012/0071926 A1 | 3/2012 | Jani et al. | |
| 2012/0083845 A1 | 4/2012 | Winslow et al. | |
| 2012/0095512 A1 | 4/2012 | Nihalani | |
| 2012/0130436 A1 | 5/2012 | Haskins et al. | |
| 2012/0158064 A1 | 6/2012 | Kroll | |
| 2012/0203278 A1 | 8/2012 | Gil et al. | |
| 2012/0221053 A1 | 8/2012 | Copf | |
| 2012/0226316 A1 | 9/2012 | Dant et al. | |
| 2012/0232593 A1 | 9/2012 | Predick | |
| 2012/0232595 A1 | 9/2012 | Holschlag | |
| 2012/0259369 A1 | 10/2012 | Hammer | |
| 2012/0290013 A1 | 11/2012 | Simonson | |
| 2012/0296335 A1 | 11/2012 | Mullaney | |
| 2012/0303062 A1 | 11/2012 | Amstutz et al. | |
| 2013/0018422 A1 | 1/2013 | Rinner et al. | |
| 2013/0030468 A1 | 1/2013 | Le Couedic et al. | |
| 2013/0079826 A1 | 3/2013 | Simonson | |
| 2013/0085534 A1 | 4/2013 | Hainard et al. | |
| 2013/0096617 A1 | 4/2013 | Ballard et al. | |
| 2013/0123854 A1 | 5/2013 | Kondrashov et al. | |
| 2013/0211457 A1 | 8/2013 | Dickinson et al. | |
| 2013/0253588 A1 | 9/2013 | Traynelis et al. | |
| 2013/0268004 A1 | 10/2013 | Rathbun | |
| 2013/0274807 A1 | 10/2013 | Prajapati | |
| 2013/0274808 A1 | 10/2013 | Larroque-Lahitette et al. | |
| 2014/0018858 A1 | 1/2014 | Laeng et al. | |
| 2014/0066990 A1 | 3/2014 | Akbarnia et al. | |
| 2014/0088650 A1 | 3/2014 | Taddia et al. | |
| 2014/0114359 A1 | 4/2014 | Hawkes | |
| 2014/0135839 A1 | 5/2014 | Frankel et al. | |
| 2014/0148856 A1 | 5/2014 | Ibarra et al. | |
| 2014/0222076 A1 | 8/2014 | Jackson | |
| 2014/0249581 A1 | 9/2014 | Stachniak | |

(56) References Cited

U.S. PATENT DOCUMENTS

| | | |
|---|---|---|
| 2014/0277146 A1 | 9/2014 | Li et al. |
| 2014/0277160 A1 | 9/2014 | Ziolo |
| 2014/0277163 A1 | 9/2014 | Kretzer et al. |
| 2014/0303674 A1 | 10/2014 | Sasing |
| 2014/0316468 A1 | 10/2014 | Keiser et al. |
| 2014/0336706 A1 | 11/2014 | Garamszegi |
| 2014/0343613 A1 | 11/2014 | Eliasen et al. |
| 2015/0032160 A1 | 1/2015 | Carbone et al. |
| 2015/0057707 A1 | 2/2015 | Barrus et al. |
| 2015/0057708 A1 | 2/2015 | Ballard et al. |
| 2015/0073479 A1 | 3/2015 | Rinner |
| 2015/0094769 A1 | 4/2015 | Abbasi |
| 2015/0119941 A1 | 4/2015 | Daniels et al. |
| 2015/0190178 A1 | 7/2015 | McCarthy et al. |
| 2015/0196328 A1 | 7/2015 | Hirschl et al. |
| 2015/0223844 A1 | 8/2015 | Leff et al. |
| 2015/0230830 A1 | 8/2015 | Frankel et al. |
| 2015/0282842 A1 | 10/2015 | Beyar et al. |
| 2015/0313645 A1 | 11/2015 | Hansell |
| 2015/0359568 A1 | 12/2015 | Rezach |
| 2016/0135846 A1 | 5/2016 | Mirda |
| 2016/0143665 A1 | 5/2016 | Biedermann et al. |
| 2016/0166289 A1 | 6/2016 | Alsup et al. |
| 2016/0287294 A1 | 10/2016 | Kubo et al. |
| 2017/0020578 A1 | 1/2017 | Mosnier et al. |
| 2017/0079690 A1 | 3/2017 | Oberlander et al. |
| 2017/0086885 A1 | 3/2017 | Duncan et al. |
| 2017/0086895 A1 | 3/2017 | Barra et al. |
| 2017/0095271 A1 | 4/2017 | Faulhaber |
| 2017/0105764 A1 | 4/2017 | Williams |
| 2017/0112540 A1 | 4/2017 | Montello et al. |
| 2017/0119439 A1 | 5/2017 | Ozdil et al. |
| 2017/0128105 A1 | 5/2017 | Patrinicola et al. |
| 2017/0128107 A1 | 5/2017 | Alsup et al. |
| 2017/0209182 A1 | 7/2017 | Picetti et al. |
| 2017/0245900 A1 | 8/2017 | Rezach |
| 2017/0281247 A1 | 10/2017 | Murray et al. |
| 2017/0311985 A1 | 11/2017 | Bobbitt et al. |
| 2017/0333087 A1 | 11/2017 | Lee et al. |
| 2017/0333088 A1 | 11/2017 | Lee et al. |
| 2017/0348026 A1 | 12/2017 | Stein et al. |
| 2018/0042647 A1 | 2/2018 | Cowan et al. |
| 2018/0098798 A1 | 4/2018 | Italiaie et al. |
| 2018/0116695 A1 | 5/2018 | Armstrong et al. |
| 2018/0161073 A1 | 6/2018 | Lee et al. |
| 2018/0168694 A1 | 6/2018 | Lee et al. |
| 2018/0195150 A1 | 7/2018 | Meyer et al. |
| 2018/0206890 A1 | 7/2018 | Rezach |
| 2018/0228516 A1 | 8/2018 | Armstrong et al. |
| 2018/0228518 A1 | 8/2018 | Carruth et al. |
| 2018/0243009 A1 | 8/2018 | Bobbitt et al. |
| 2018/0280062 A1 | 10/2018 | Lee et al. |
| 2018/0280063 A1 | 10/2018 | Lee et al. |
| 2018/0317972 A1 | 11/2018 | Abbasi |
| 2019/0167313 A1 | 6/2019 | Ortiz et al. |
| 2019/0175226 A1 | 6/2019 | Carruth et al. |
| 2019/0183541 A1 | 6/2019 | Lee et al. |
| 2019/0269440 A1 | 9/2019 | Patrinicola et al. |
| 2019/0336178 A1 | 11/2019 | Finn et al. |
| 2019/0365432 A1 | 12/2019 | Lee et al. |
| 2020/0060729 A1 | 2/2020 | Lee et al. |
| 2020/0069341 A1 | 3/2020 | Abbasi |
| 2020/0170695 A1 | 6/2020 | Lee et al. |
| 2021/0068872 A1 | 3/2021 | Carruth et al. |
| 2021/0186572 A1 | 6/2021 | Lee et al. |
| 2022/0039835 A1 | 2/2022 | Lee et al. |

FOREIGN PATENT DOCUMENTS

| | | |
|---|---|---|
| EP | 1857064 A1 | 11/2007 |
| EP | 2 319 436 A1 | 5/2011 |
| EP | 2730242 A1 | 5/2014 |
| JP | H09-503148 A | 3/1997 |
| JP | 2001517122 A | 10/2001 |
| JP | 2003515380 A | 5/2003 |
| JP | 2003526442 A | 9/2003 |
| JP | 2007530223 A | 11/2007 |
| JP | 2008523890 A | 7/2008 |
| JP | 2009522021 A | 6/2009 |
| JP | 2009533087 A | 9/2009 |
| JP | 2010506670 A | 3/2010 |
| JP | 2010540112 A | 12/2010 |
| JP | 2014097405 A | 5/2014 |
| JP | 2014521383 A | 8/2014 |
| JP | 2016501690 A | 1/2016 |
| KR | 20100054713 A | 5/2010 |
| WO | 2005/044119 A2 | 5/2005 |
| WO | 2007124242 A1 | 11/2007 |
| WO | 2009076107 A1 | 6/2009 |
| WO | 2009/110865 A8 | 12/2009 |
| WO | 2011/004222 A1 | 1/2011 |
| WO | 2011/006155 A1 | 1/2011 |
| WO | 2015/017250 A1 | 2/2015 |

OTHER PUBLICATIONS

U.S. Appl. No. 15/377,449, filed Dec. 13, 2016, Implant Adaptors and Related Methods.
U.S. Appl. No. 15/382,837, filed Dec. 19, 2016, Offset Rods, Offset Rod Connectors, and Related Methods.
U.S. Appl. No. 15/284,587, filed Oct. 4, 2016, Implant Connectors and Related Methods.
U.S. Appl. No. 15/430,188, filed Feb. 10, 2017, Tandem Rod Connectors and Related Methods.
U.S. Appl. No. 15/471,075, filed Mar. 28, 2017, Articulating Implant Connectors and Related Methods.
U.S. Appl. No. 15/828,805, filed Dec. 1, 2017, Rod-to-Rod Connectors Having Robust Rod Closure Mechanisms and Related Methods.
U.S. Appl. No. 15/843,618, filed Dec. 15, 2017, Unilateral Implant Holders and Related Methods.
U.S. Appl. No. 15/926,051, filed Mar. 20, 2018, Articulating Implant Connectors and Related Methods.
U.S. Appl. No. 16/280,918, filed Feb. 20, 2019, Tandem Rod Connectors and Related Methods.
U.S. Appl. No. 16/443,849, filed Jun. 17, 2019, Implant Connectors and Related Methods.
**[No. Author Listed] VuePoint II Technique Guide, 2015, NuVasive®, Inc.; 64 pages.
**International Search Report and Written Opinion for Application No. PCT/US2017/031883, dated Aug. 2, 2017 (15 pgs).
**Invitation to Pay Additional Fees for Application No. PCT/US2018/017034, mailed May 18, 2018 (18 pages).
**International Search Report and Written Opinion for Application No. PCT/US2018/024731, dated Jul. 2, 2018 (17 pages).
**Akbarnia, B., et al., "Pediatric Isola® Prebent Rod Placement," (Technique Manual), DePuy Acromed, Oct. 2010; 2 pages.
**International Search Report and Written Opinion for Application No. PCT/US2018/062786, dated Feb. 4, 2019 (15 pages).
U.S. Appl. No. 16/666,887, filed Oct. 29, 2019, Offset Rods, Offset Rod Connectors, and Related Methods.
U.S. Appl. No. 16/782,030, filed Feb. 4, 2020, Articulating Implant Connectors and Related Methods.
Japanese Office Action for Application No. 2018-560664, dated Apr. 21, 2021 (6 pages) Translation Only.
U.S. Appl. No. 17/191,667, filed Mar. 3, 2021, Articulating Implant Connectors and Related Methods.
International Search Report and Written Opinion for Application No. PCT/US2018/017034, dated Aug. 1, 2018 (20 pages).
Chinese Office Action for Application No. 201780030641 3, dated Nov. 1, 2021 (15 pages).
Japanese Office Action for Application No. 2019-543334, dated Nov. 9, 2021 (16 pages).
Japanese Office Action for Application No. 2019-553450, dated Dec. 14, 2021 (19 pages).

(56) References Cited

OTHER PUBLICATIONS

Chinese Search Report for Application No. 201880023022.6, dated Jul. 7, 2022 (5 pages).

* cited by examiner

IMPLANT CONNECTORS AND RELATED METHODS

CROSS-REFERENCE TO RELATED APPLICATIONS

This application is a continuation of application Ser. No. 15/158,127, filed May 18, 2016, which is hereby incorporated by reference in its entirety.

FIELD

Implant connectors and related methods are disclosed herein.

BACKGROUND

Fixation systems can be used in orthopedic surgery to maintain a desired spatial relationship between multiple bones or bone fragments. For example, various conditions of the spine, such as fractures, deformities, and degenerative disorders, can be treated by attaching a spinal fixation system to one or more vertebrae. Such systems typically include a spinal fixation element, such as a rigid or flexible rod or plate, that is coupled to the vertebrae by attaching the element to various anchoring devices, such as screws, hooks, or wires. Once installed, the fixation system holds the vertebrae in a desired position until healing or spinal fusion can occur, or for some other period of time.

There are many instances in which it may be desirable to connect multiple implants to each other. For example, some revision surgeries involve extending a previously-installed construct to additional vertebral levels by coupling a newly-installed spinal rod to a previously-installed rod. By way of further example, aspects of the patient's anatomy, the surgical technique used, or the desired correction may require that multiple spinal rods be connected to one another. As yet another example, coupling multiple rods to one another can improve the overall strength and stability of an implanted construct.

There can be various difficulties associated with connecting multiple implants to each other. The available space for the implanted construct can often be very limited, particularly in the cervical area of the spine. Also, manipulating and handling these relatively small implants in the surgical wound may be challenging or cumbersome for the surgeon. There is a continual need for improved implant connectors and related methods.

SUMMARY

Implant connectors and related methods are disclosed herein. In some embodiments, a connector can include a low-profile portion to facilitate use of the connector in surgical applications where space is limited. In some embodiments, a connector can include a biased rod-pusher to allow the connector to "snap" onto a rod and/or to "drag" against the rod, e.g., for provisional positioning of the connector prior to locking.

In some embodiments, a connector includes a body that defines first and second rod-receiving recesses, the body having proximal and distal ends that define a proximal-distal axis extending therebetween; a rod pusher slidably disposed within a tunnel formed in the body and configured to translate with respect to the body along a rod pusher axis; a nut configured to translate within a cavity formed in the body along the rod pusher axis; a bias element configured to bias the nut and the rod pusher along the rod pusher axis towards the first rod-receiving recess; a first set screw threadably received in the nut to lock a first rod within the first rod-receiving recess; and a second set screw threadably received in the body to lock a second rod within the second rod-receiving recess.

The nut can be coupled to the rod pusher. The second rod-receiving recess can be defined by a pair of spaced apart arms of the body. The nut can include a pair of spaced apart arms aligned with the arms of the body. The first rod-receiving recess can be open in a distal direction. The second rod-receiving recess can be open in a proximal direction. The rod pusher axis can be substantially perpendicular to the proximal-distal axis. The first rod-receiving recess can be formed in a wing portion of the body, the wing portion having a height dimension extending parallel to a longitudinal axis of the first rod-receiving recess. The height of the wing portion can be less than about 5 mm. The first rod-receiving recess can be formed in a wing portion of the body, the wing portion having a height dimension extending parallel to a longitudinal axis of the first rod-receiving recess. A ratio of the height of the wing portion to a diameter of the first rod-receiving recess can be less than about 2:1. The bias element can include a C-shaped spring clip. The spring clip can be at least partially received within a groove formed in the cavity of the body and a groove formed in the nut. The groove formed in the cavity of the body can have a first end with a smaller radius of curvature and a second end with a larger radius of curvature. A diameter of the first end of the groove can be less than a resting diameter of the spring clip. The connector can have a resting configuration in which the spring clip is disposed in the second end of the groove and no rod is disposed in the first rod-receiving recess. Insertion of a first rod into the first rod-receiving recess can displace the rod-pusher and the nut along the rod pusher axis to move the spring clip towards the first end of the groove such that the spring clip urges the rod pusher against the first rod. The bias element can urge the rod pusher against the rod before the first set screw is tightened. Tightening the first set screw within the nut can cause a surface of the first set screw to bear against the interior of a recess formed in the body to urge the nut and the rod pusher towards the first rod-receiving recess and to lock a first rod therein. The rod pusher can exert a drag force on a first rod when the first rod is disposed in the first rod-receiving recess. The connector can provide tactile feedback when a first rod is snapped into the first rod-receiving recess.

In some embodiments, a connector includes a body that defines first and second rod-receiving recesses, the body having proximal and distal ends that define a proximal-distal axis extending therebetween; a first locking element configured to lock a first rod within the first rod-receiving recess, the first locking element being disposed distal to the second rod-receiving recess; and a second locking element configured to lock a second rod within the second rod-receiving recess, the second locking element being disposed proximal to the second rod-receiving recess.

The first and second locking elements can be first and second set screws each having a rotation axis that is parallel to the proximal-distal axis.

In some embodiments, a method of connecting first and second spinal rods includes positioning a first spinal rod within a first rod-receiving recess formed in a body portion of a connector; tightening a first set screw within a nut to translate the nut within the body towards the first rod-receiving recess and thereby urge a rod pusher against the first spinal rod to lock the first spinal rod to the connector;

positioning a second spinal rod within a second rod-receiving recess formed in the body portion of the connector; and tightening a second set screw within the body to lock the second spinal rod to the connector.

The method can include hooking a wing portion of the connector onto the first rod at a location between two bone anchors to which the first rod is coupled, the two bone anchors being implanted in adjacent vertebral levels of a patient's spine. Positioning the first spinal rod within the first rod-receiving recess can include displacing the rod pusher away from the first rod-receiving recess and compressing a spring clip into a reduced-diameter portion of a groove formed in the body such that the rod pusher exerts a drag force on the first rod before the first set screw is tightened. Tightening the first set screw can include contacting a ramped surface of the set screw with a corresponding ramped surface of a recess formed in the body portion of the connector.

In some embodiments, a connector includes a body that defines first and second rod-receiving recesses, the body having proximal and distal ends that define a proximal-distal axis extending therebetween; a rod pusher slidably disposed within a tunnel formed in the body and configured to translate with respect to the body along a rod pusher axis; a bias element configured to bias the rod pusher along the rod pusher axis towards the first rod-receiving recess; and a set screw threadably received in the body to lock a first rod within the first rod-receiving recess and to lock a second rod within the second rod-receiving recess.

The rod pusher can include a first bearing surface configured to contact and bear against a first rod disposed in the first rod-receiving recess and a second bearing surface configured to contact and bear against a second rod disposed in the second rod-receiving recess. The connector can include a saddle disposed in a cavity formed in the body. The saddle can be translatable along the proximal-distal axis of the body. The saddle can include a ramped bearing surface configured to contact and bear against a corresponding ramped bearing surface of the rod pusher. Movement of the saddle along the proximal-distal axis can be effective to move the rod pusher along the rod pusher axis. The first rod-receiving recess can be open in a distal direction. The second rod-receiving recess can be open in a proximal direction. The rod pusher axis can be substantially perpendicular to the proximal-distal axis. The bias element can include a spring wire received within a through-bore formed in the body and a through-bore formed in the rod pusher. The through-bore in the rod pusher can include a cylindrical middle portion and opposed end portions that are elongated in the direction of the rod pusher axis. The tunnel can extend between the first rod-receiving recess and the second rod-receiving recess. The first rod-receiving recess can be formed in a wing portion of the body, the wing portion having a height dimension extending parallel to a longitudinal axis of the first rod-receiving recess. A ratio of the height of the wing portion to a diameter of the first rod-receiving recess can be less than about 2:1. The connector can have a resting configuration in which the bias element is in a resting position and no rod is disposed in the first rod-receiving recess. Insertion of a rod into the first rod-receiving recess can displace the rod-pusher along the rod pusher axis to bend the bias element away from its resting position such that the bias element urges the rod pusher against the rod before the set screw is tightened. Tightening the set screw within the body can cause a surface of the set screw to bear against a second rod disposed in the second rod-receiving recess to urge the rod pusher towards the first rod-receiving recess and to lock a first rod in the first rod-receiving recess. The rod pusher can exert a drag force on a rod when the rod is disposed in the first rod-receiving recess. The connector can provide tactile feedback when a rod is snapped into the first rod-receiving recess. The second rod-receiving recess can have a relief disposed in alignment with the end of the tunnel such that the rod pusher protrudes into the second rod-receiving recess. The second rod-receiving recess can be asymmetrical about the proximal-distal axis. The second rod-receiving recess can be configured such that, as a rod is seated within the second rod-receiving recess, the rod translates distally along the proximal-distal axis and laterally along the rod pusher axis.

In some embodiments, a connector includes a body that defines first and second rod-receiving recesses, the body having proximal and distal ends that define a proximal-distal axis extending therebetween; a rod pusher disposed within a tunnel formed in the body and configured to rotate with respect to the body about a pivot axis; and a set screw threadably received in the body to lock a second rod within the second rod-receiving recess and to thereby pivot the rod pusher to lock a first rod within the first rod-receiving recess.

In some embodiments, a method of connecting first and second spinal rods includes positioning a first spinal rod within a first rod-receiving recess formed in a body portion of a connector; positioning a second spinal rod within a second rod-receiving recess formed in the body portion of the connector; and tightening a set screw within the body to press the second rod against a rod pusher, thereby urging the rod pusher against the first spinal rod to lock the first and second spinal rods to the connector.

The method can include hooking a wing portion of the connector onto the first rod at a location between two bone anchors to which the first rod is coupled, the two bone anchors being implanted in adjacent vertebral levels of a patient's spine. Tightening the set screw can simultaneously lock both the first and second rods to the connector.

In some embodiments, a connector includes a body that defines a first rod-receiving recess, the body having proximal and distal ends that define a proximal-distal axis extending therebetween; a rod pusher disposed within a tunnel formed in the body, the tunnel extending along a tunnel axis; a bias element configured to bias the rod pusher towards the first rod-receiving recess; and a first set screw threadably received in a proximal end of the tunnel to lock a first rod within the first rod-receiving recess.

The bias element can include a leaf spring disposed within a through-bore formed in the body. A projection of the rod pusher can be received within a keyed opening of the leaf spring to retain the rod pusher within the body. The bias element can include a spring wire that extends through a through-bore formed in the body and a through-bore formed in the rod pusher. The through-bore in the rod pusher can include a cylindrical middle portion and opposed end portions that are elongated in the direction of the tunnel axis. The rod pusher can be translatable along the tunnel axis. The tunnel axis can be substantially parallel to the proximal-distal axis. The rod pusher can be rotatable about a pivot axis that extends perpendicular to the tunnel axis. The body can define a second rod-receiving recess. The connector can include a second set screw threadably received in the body to lock a second rod within the second rod-receiving recess. The first rod-receiving recess can be open in a lateral direction. The second rod-receiving recess can be open in a proximal direction. The tunnel can extend between the first rod-receiving recess and a proximal-facing surface of the body portion of the connector. The connector can have a resting configuration in which no rod is disposed in the first rod-receiving recess and the bias element urges the rod pusher distally towards the first rod-receiving recess. Insertion of a rod into the first rod-receiving recess can displace the rod-pusher along the tunnel axis to bend the bias element away from its resting position such that the bias element urges the rod pusher against the rod before the first set screw is tightened. Tightening the first set screw within the tunnel can cause a surface of the set screw to bear against the rod pusher and thereby urge the rod pusher towards the first rod-receiving recess to lock a rod disposed therein to the connector. The rod pusher can exert a drag force on a rod when the rod is disposed in the first rod-receiving recess. The connector can provide tactile feedback when a rod is snapped into the first rod-receiving recess.

In some embodiments, a method of connecting first and second spinal rods includes positioning a first spinal rod within a first rod-receiving recess formed in a body portion of a connector; and tightening a first set screw within a tunnel formed in the connector to urge a rod pusher disposed in the tunnel against the first spinal rod, thereby locking the first spinal rod to the connector. A bias element of the connector can cause the rod pusher to exert a drag force on the first rod before the first set screw is tightened.

BRIEF DESCRIPTION OF THE DRAWINGS

FIG. 2I is a side view of the connector of FIG. 2A coupled to first and second spinal rods.

DETAILED DESCRIPTION

Figure 1A:
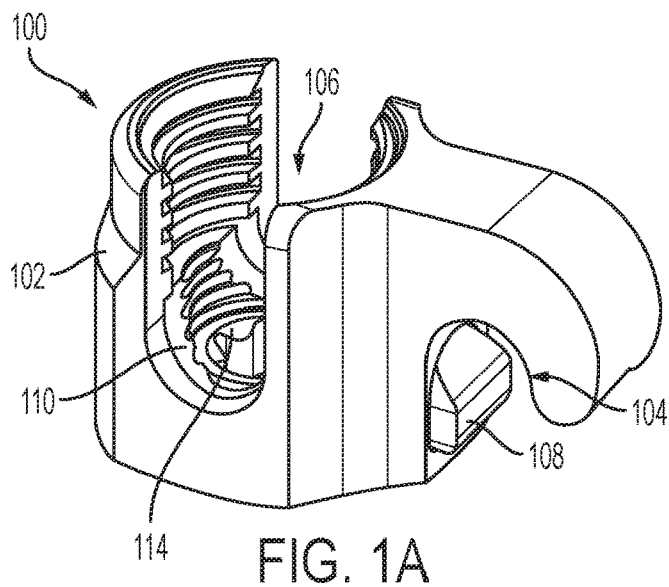
FIG. 1A is a perspective view of a connector.
Figure 1B:
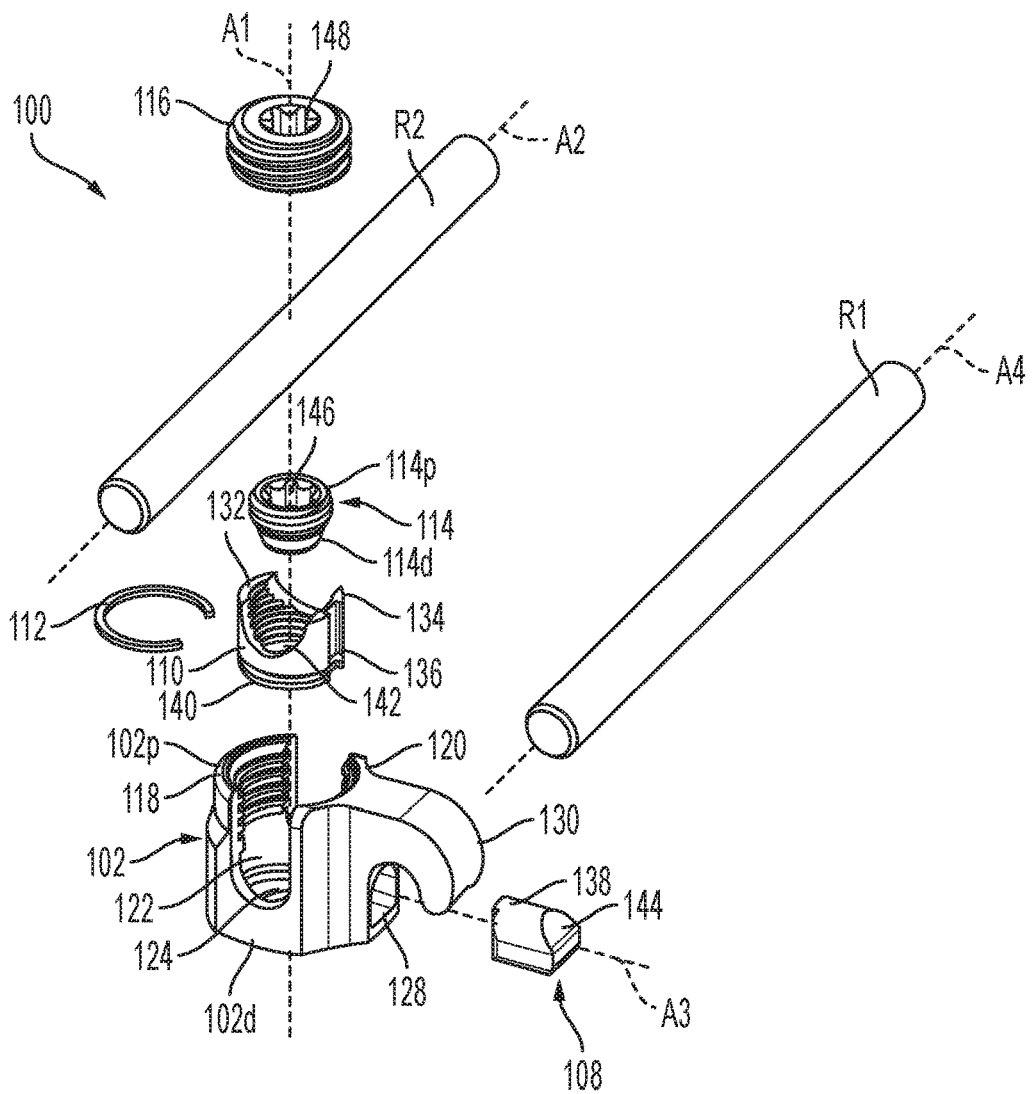
FIG. 1B is an exploded perspective view of the connector of FIG. 1A shown with first and second spinal rods.
Figure 1C:
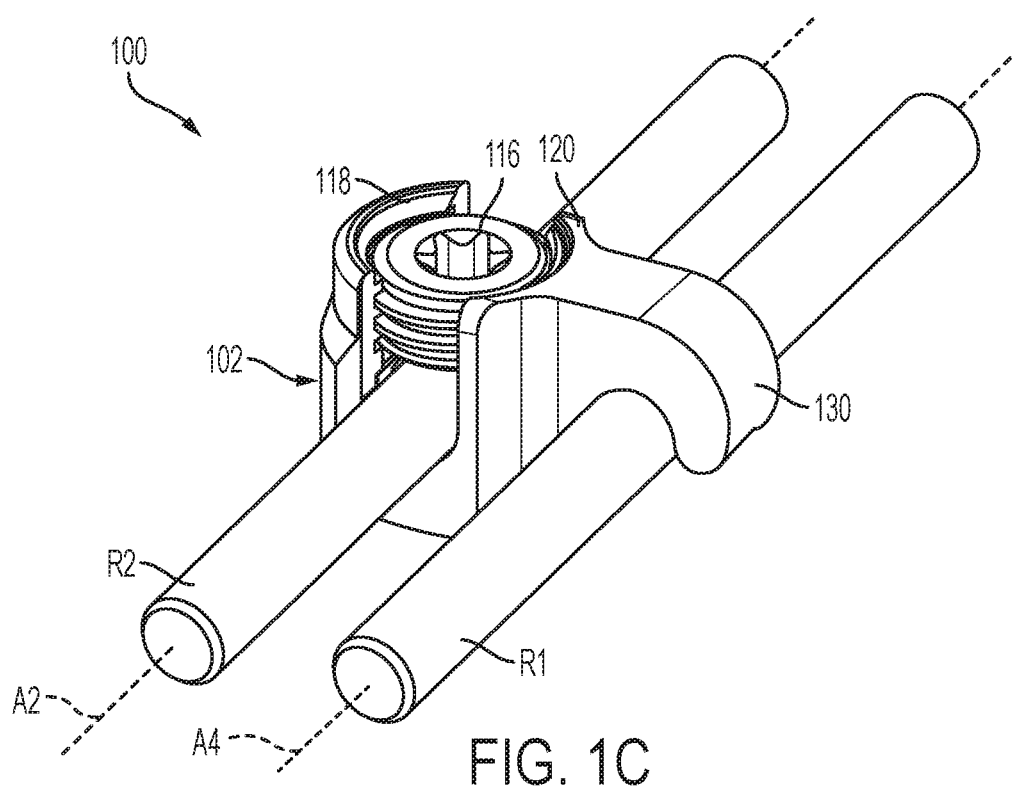
FIG. 1C is a perspective view of the connector of FIG. 1A coupled to first and second spinal rods.

Implant connectors and related methods are disclosed herein. In some embodiments, a connector can include a low-profile portion to facilitate use of the connector in surgical applications where space is limited. In some embodiments, a connector can include a biased rod-pusher to allow the connector to "snap" onto a rod and/or to "drag" against the rod, e.g., for provisional positioning of the connector prior to locking.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

FIGS. 1A-1J illustrate an exemplary embodiment of a connector 100. As shown, the connector 100 can include a body 102 that defines first and second rod-receiving recesses 104, 106, a rod pusher 108, a nut 110, a bias element or spring clip 112, a first locking element or set screw 114, and a second locking element or set screw 116. The nut 110 can be configured to translate laterally within the body 102, and can be biased by the spring clip 112 in a direction that urges the rod pusher 108 into a first rod R1 disposed in the first rod-receiving recess 104. The first set screw 114 can be tightened to lock the connector 100 to the first rod R1. The second set screw 116 can be tightened to lock a second rod R2 in the second rod-receiving recess 106 of the connector 100. The illustrated connector 100 can thus allow for independent locking of first and second rods R1, R2 to the connector. The connector 100 can include one or more low-profile portions to facilitate use in tight spaces. For example, the first rod-receiving recess 104 can be formed in a portion of the connector body 102 having a reduced-profile, e.g., to fit between bone anchors implanted in adjacent levels of the cervical spine.

The body 102 can include proximal and distal ends 102p, 102d that define a proximal-distal axis A1. The proximal end 102p of the body 102 can include a pair of spaced apart arms 118, 120 that define the second rod-receiving recess 106 therebetween. A rod R2 disposed in the second rod-receiving recess 106 can have a central longitudinal rod axis A2. The second rod-receiving recess 106 can be open in a proximal direction, such that a rod R2 can be inserted into the recess by moving the rod distally with respect to the connector 100. Each of the arms 118, 120 can extend from the distal portion 102d of the body 102 to a free end. The outer surfaces of each of the arms 118, 120 can include a feature (not shown), such as a recess, dimple, notch, projection, or the like, to facilitate coupling of the connector 100 to various instruments. For example, the outer surface of each arm 118, 120 can include an arcuate groove at the respective free end of the arms for attaching the connector 100 to an extension tower or retractor. The arms 118, 120 can include or can be coupled to extension or reduction tabs (not shown) that extend proximally from the body 102 to functionally extend the length of the arms 118, 120. The extension tabs can facilitate insertion and reduction of a rod or other implant, as well as insertion and locking of the set screw 116. The extension tabs can be configured to break away or otherwise be separated from the arms 118, 120. The inner surfaces of each of the arms 118, 120 can be configured to mate with the second set screw 116. For example, the inner surfaces of the arms 118, 120 can include threads that correspond to external threads formed on the second set screw 116. Accordingly, rotation of the second set screw 116 with respect to the body 102 about the axis A1 can be effective to translate the set screw with respect to the body axially along the axis A1.

Figure 1D:
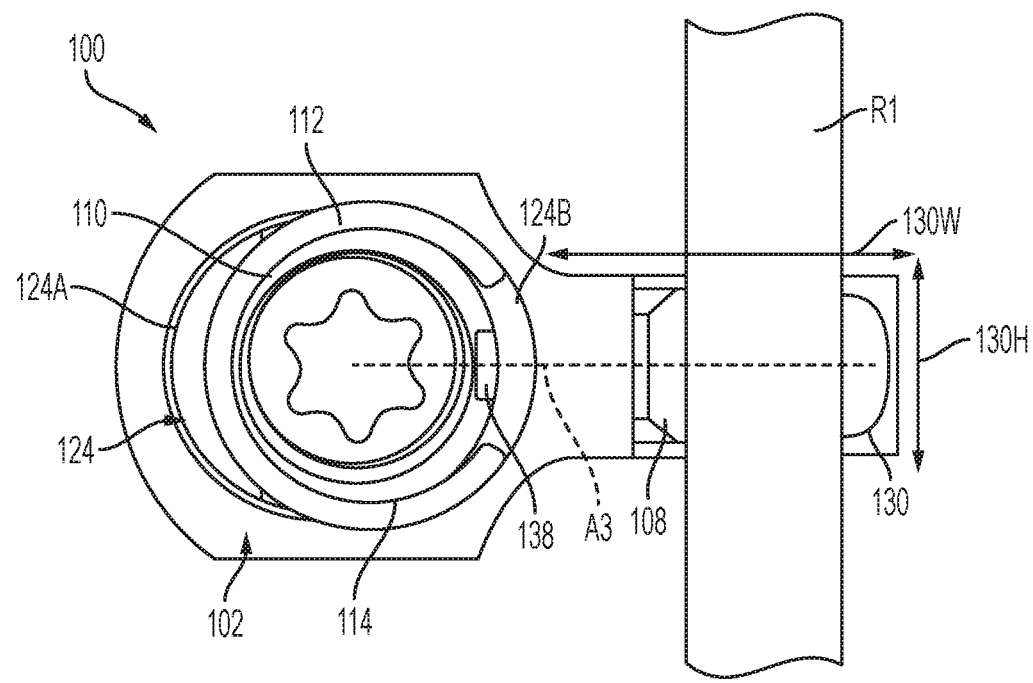
FIG. 1D is a sectional bottom view of the connector of FIG. 1A and a spinal rod.

The distal end 102d of the body 102 can define an interior cavity 122 in which the nut 110 can be disposed. At least one dimension of the cavity 122 can be greater than a corresponding dimension of the nut 110 to allow the nut to translate within the cavity along a rod pusher axis A3. The axis A3 can be perpendicular or substantially perpendicular to the axis A1. The axis A3 can also be perpendicular or substantially perpendicular to the axis A2. In the illustrated embodiment, the cavity 122 has an oval-shaped cross section. An undercut groove 124 can be formed in the cavity 122 to receive at least a portion of the spring clip 112. As shown in FIG. 1D, the cross section of the groove 124 can be substantially elliptical with different sized curvatures at each end of the major axis of the ellipse. A first end 124A of the groove 124 can have a relatively smaller radius of curvature and a second, opposite end 124B of the groove 124 can have a relatively larger radius of curvature. Curved transition portions of the groove 124 can extend between the first and second ends 124A, 124B, such that the groove is generally egg-shaped in cross section. The diameter of the first end 124A of the groove can be less than the resting diameter of the spring clip 112, such that the spring clip's tendency to expand towards its resting diameter urges the spring clip and, by extension, the nut 110 and the rod pusher 108, along the axis A3 towards the first rod-receiving recess 104. The diameter of the second end 124B of the groove 124 can be greater than, equal to, or slightly less than the resting diameter of the spring clip 112.

Figure 1E:
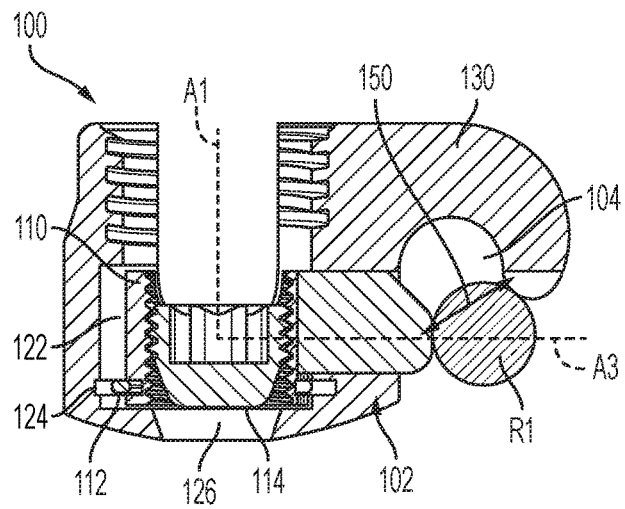
FIG. 1E is a sectional side view of the connector of FIG. 1A in a first configuration.

A recess 126 sized to receive at least a portion of the first set screw 114 can be formed in the body 102, as shown for example in FIG. 1E. The recess 126 can be formed distal to the cavity 122. The recess 126 can be frustoconical as shown to provide a ramped bearing surface for engagement with the distal end of the first set screw 114. In other embodiments, the recess 126 can be cylindrical or can have other shapes.

A tunnel 128 can be formed in the body 102 and can extend along the axis A3 between the cavity 122 and the first rod-receiving recess 104. The tunnel 128 can have a shape that is substantially a negative of the exterior shape of the rod pusher 108. The rod pusher 108 can be slidably disposed within the tunnel 128 such that the rod pusher can translate along the axis A3 with respect to the body 102.

The body 102 can include a cantilevered wing portion 130 that defines the first rod-receiving recess 104. A rod R1 disposed in the first rod-receiving recess 104 can have a central longitudinal rod axis A4. The axis A4 can be parallel to the axis A2 as shown, or can be perpendicular or obliquely angled with respect to the axis A2. The wing portion 130 can extend radially-outward from the second arm 120 of the body 102. The wing portion 130 can have a width 130W and a height 130H. A ratio of the width 130W to the diameter of the first rod-receiving recess 104 (or of a rod R1 disposed therein) can be less than about 1.5:1, less than about 2:1, and/or less than about 3:1. A ratio of the height 130H to the diameter of the first rod-receiving recess 104 (or of a rod R1 disposed therein) can be less than about 0.5:1, less than about 1:1, and/or less than about 2:1. In some embodiments, the height 130H can be less than about 5 mm, less than about 4 mm, and/or less than about 3 mm. The first rod-receiving recess 104 can be open in a distal direction such that a rod R1 can be inserted into the recess by moving the connector 100 distally with respect to the rod. In other embodiments, the first rod-receiving recess 104 can be open in a proximal direction, e.g., by flipping the wing portion 130 and forming it such that it extends from a distal portion of the body 102, or open in a lateral direction.

The nut 110 can be positioned within the cavity 122 formed in the body 102. The nut 110 can be sized such that it is laterally translatable within the cavity 122, along the axis A3. The nut 110 can be generally cylindrical with first and second arms 132, 134 extending in a proximal direction to respective free ends of the arms. The first and second arms 132, 134 can be aligned with the first and second arms 118, 120 of the body 102 such that a recess defined therebetween is aligned with the second rod-receiving recess 106. Accordingly, the second rod R2 can be simultaneously cradled between the arms 132, 134 of the nut 110 and the arms 118, 120 of the body 102 when the rod is disposed in the second rod-receiving recess 106.

The nut 110 can include a mating feature configured to couple the nut to the rod pusher 108. For example, the nut can include a dovetail groove 136 formed in an exterior surface thereof sized to receive a corresponding dovetail projection 138 formed on the rod pusher 108. The mating feature can be configured to prevent movement of the rod pusher 108 with respect to the nut 110 along the axis A3, while still allowing movement of the rod pusher with respect to the nut along the axis A1. Accordingly, the nut 110 can be assembled to the rod pusher 108 and the body 102 by inserting the rod pusher through the tunnel 128 along the axis A3 such that the dovetail projection 138 extends into the cavity 122 of the body 102, and then lowering the nut distally into the cavity along the axis A1, with the projection 138 of the rod pusher 108 sliding into the groove 136 of the nut as the nut is advanced into the cavity. It will be appreciated that the groove can alternatively be formed in the rod pusher 108 and the projection formed on the nut 110. It will further be appreciated that the nut 110 can be formed integrally with the rod pusher 108, or mated to the rod pusher in other ways.

The nut 110 can include an annular groove 140 formed in an exterior surface thereof sized to receive at least a portion of the spring clip 112. When the connector 100 is assembled, the spring clip 112 can extend partially into the groove 124 formed in the cavity 122 and partially into the groove 140 formed in the nut 110 to retain the nut within the cavity.

The nut 110 can define a central opening 142 that extends completely through the nut along the axis A1. The inner surface of the opening 142 can be configured to mate with the first set screw 114. For example, the inner surface 142 can include threads that correspond to external threads formed on the first set screw 114. Accordingly, rotation of the first set screw 114 with respect to the nut 110 about the axis A1 can be effective to translate the set screw with respect to the nut axially along the axis A1.

As noted above, the rod pusher 108 can be slidably disposed within the tunnel 128 of the body 102 and can be configured to translate with respect to the body along the axis A3. The rod pusher 108 can include a bearing surface 144 configured to contact and bear against a rod R1 disposed in the first rod-receiving recess 104. The bearing surface 144 can extend at an oblique angle with respect to a longitudinal axis of the rod pusher 108 such that the bearing surface is ramped. The bearing surface 144 can be planar as shown, or can be convex, concave, pointed, sharpened, etc. For example, the bearing surface 144 can be concave and can define a section of a cylinder, such that the bearing surface matches or approximates the contour of a cylindrical rod R1 disposed in the first rod-receiving recess 104. The rod pusher 108 can include a projection 138 or other mating feature, as described above, for mating the rod pusher to the nut 110.

The bias element can be configured to bias the nut 110 and the rod pusher 108 towards the first rod-receiving recess 104. In the illustrated embodiment, the bias element is a C-shaped spring clip 112. The spring clip 112 can be formed from a resilient material such that, when radially-compressed, the spring clip tends to expand radially-outward towards its resting diameter. Accordingly, when compressed into the groove 124 formed in the cavity 122, the spring clip 112 can exert a radial-outward force against the walls of the groove and can tend to urge the nut 110 and the rod pusher 108 towards the first rod-receiving recess 104. While a C-shaped spring clip 112 is shown, various other bias elements can be used instead or in addition, such as leaf springs, wire springs, wave springs, coil springs, and the like.

The first set screw 114 can include a proximal portion 114p and a distal portion 114d. The proximal portion 114p of the first set screw 114 can include an exterior thread configured to mate with the interior threads of the nut 110 to allow the first set screw to be advanced or retracted along the axis A1 with respect to the nut by rotating the first set screw about the axis A1. The proximal portion 114p of the first set screw 114 can include a driving interface 146 configured to receive a driver for applying a rotational force to the first set screw about the axis A1. The distal portion 114d of the first set screw 114 can define a bearing surface configured to contact and bear against the recess 126 formed in the body 102. In the illustrated embodiment, the distal portion 114d of the first set screw 114 defines a frustoconical ramped bearing surface that corresponds to the ramped bearing surface of the recess 126. While a first set screw 114 is shown, it will be appreciated that other locking elements can be used instead or addition, such as a closure cap that advances and locks by quarter-turn rotation, a closure cap that slides in laterally without rotating, and so forth.

The second set screw 116 can include an exterior thread configured to mate with the interior threads formed on the arms 118, 120 of the body 102 to allow the second set screw to be advanced or retracted along the axis A1 with respect to the body by rotating the second set screw about the axis A1. The second set screw 116 can include a driving interface 148 configured to receive a driver for applying a rotational force to the second set screw about the axis A1. The distal surface of the second set screw 116 can be configured to contact and bear against a rod R2 disposed in the second rod-receiving 106 recess to lock the rod to the connector 100. When tightened against the rod R2, the second set screw 116 can prevent the rod from translating relative to the connector 100 along the axis A2 and/or from rotating with respect to the connector about the axis A2. While a second set screw 116 is shown, it will be appreciated that other locking elements can be used instead or addition, such as a closure cap that advances and locks by quarter-turn rotation, a closure cap that slides in laterally without rotating, a nut that threads onto an exterior of the connector 100, and so forth.

Operation of the connector 100 is illustrated schematically in FIGS. 1E-1J.

Figure 1F:
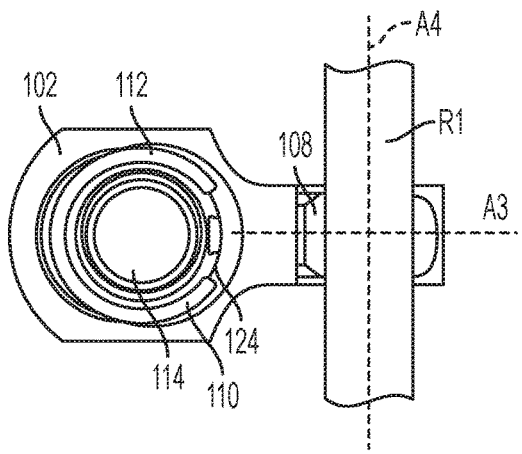
FIG. 1F is a sectional bottom view of the connector of FIG. 1A in the first configuration.

As shown in FIGS. 1E-1F, the connector 100 can have a resting configuration in which no rod is disposed in the first or second rod-receiving recesses 104, 106. In this configuration, the biasing force of the spring clip 112 can cause the spring clip to slide into the larger diameter portion 124B of the groove 124, thereby sliding the nut 110 and the rod pusher 108 towards the first rod-receiving recess 104. The first set screw 114 can be mounted in the nut 110 at this time, but not advanced far enough for the distal end 114d of the set screw to contact the recess 126 of the body 102.

Figure 1G:
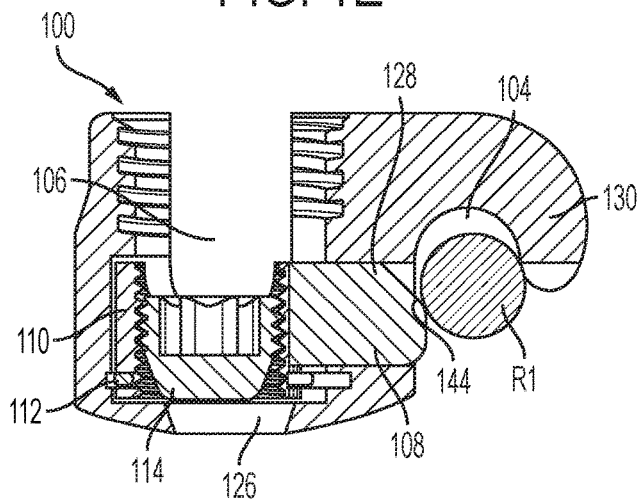
FIG. 1G is a sectional side view of the connector of FIG. 1A in a second configuration.
Figure 1H:
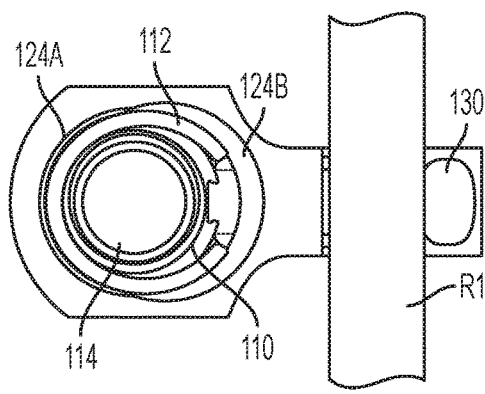
FIG. 1H is a sectional bottom view of the connector of FIG. 1A in the second configuration.

In the resting configuration, the wing portion 130 of the body 102 and the free end of the rod pusher 108 can define an aperture 150 that is smaller than the diameter of a first rod R1 to which the connector 100 is to be coupled. Accordingly, as shown in FIGS. 1G-1H, as the rod R1 is inserted into the first rod-receiving recess 104, the rod bears against the rod pusher 108 to move the connector 100 out of the resting configuration. Insertion of the rod R1 can move the rod pusher 108 and the nut 110 along the axis A3, thereby compressing the spring clip 112 towards the smaller diameter portion 124A of the groove 124. As the largest cross-sectional portion of the rod R1 is positioned in the aperture 150, the nut 110 can be displaced to its furthest distance from the first rod-receiving recess 104.

Figure 1I:
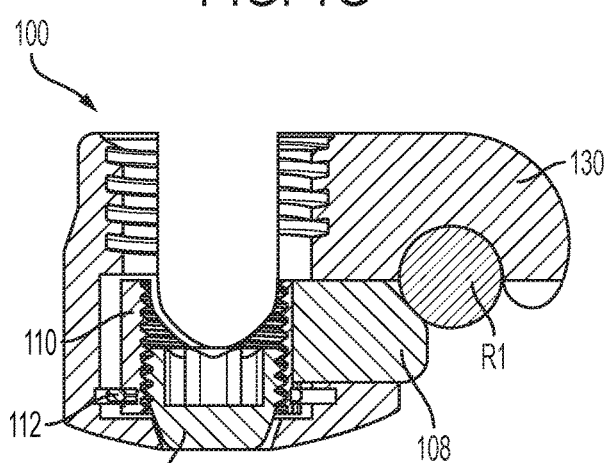
FIG. 1I is a sectional side view of the connector of FIG. 1A in a third configuration.
Figure 1J:
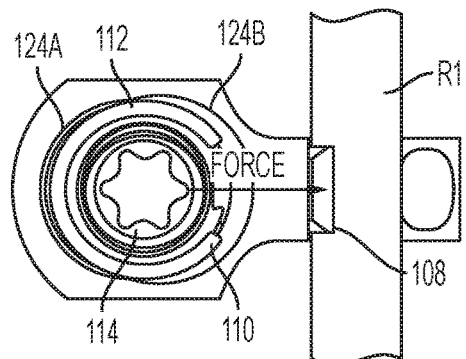
FIG. 1J is a sectional bottom view of the connector of FIG. 1A in the third configuration.

As shown in FIGS. 1I-1J, once the largest cross-sectional portion of the rod R1 clears the aperture 150 as the rod is seated in the first rod-receiving recess 104, the biasing force of the spring clip 112 can cause the nut 110 and the rod pusher 108 to move back along the axis A3 towards the first rod-receiving recess. This movement can at least partially close the aperture 150 around the rod R1 to capture the rod in the first rod-receiving recess 104. The biasing force of the spring clip 112 can resist retrograde movement of the rod pusher 108 and thus resist disconnection of the connector 100 from the first rod R1. The spring clip 112 can be at least partially compressed when the rod R1 is fully seated in the recess 104, such that the rod pusher 108 exerts a continuous drag force on the rod R1. When the connector 100 is positioned as desired with respect to the first rod R1, the first set screw 114 can be tightened within the nut 110 to lock the rod in the first rod-receiving recess 104. As the first set screw 114 is tightened, the ramped surface of the first set screw can bear against the ramped surface of the recess 126 to urge the nut 110 towards the first rod-receiving recess 104 and urge the rod pusher 108 firmly into contact with the rod R1. When the first set screw 114 is tightened, the connector 100 can be locked to the first rod R1 to resist or prevent translation of the rod R1 with respect to the connector along the axis A4 and to resist or prevent rotation of the rod R1 with respect to the connector about the axis A4. A second rod R2 can be positioned in the second rod-receiving recess 106 and the second set screw 116 can be tightened to lock the rod R2 to the body 102.

The connector 100 can thus be used to connect a first spinal rod R1 to a second spinal rod R2. While use of the connector 100 with first and second spinal rods is generally described herein, it will be appreciated that the connector can instead be configured for use with other types of orthopedic hardware, whether implanted or external. For example, one or both halves of the connector 100 can be modified to couple other various components to each other (e.g., to couple a rod to a plate, to couple a plate to a plate, to couple a rod to cable, to couple a cable to a cable, and so forth).

The connector 100 can provide various benefits for the user and/or patient. For example, the biased rod pusher 108 can provide tactile feedback when the connector 100 is "snapped" onto the first rod R1, giving the user confidence that the rod has been attached successfully before tightening the connector 100. The biased rod pusher 108 can also apply friction or "drag" to the rod R1 prior to locking the set screws 114, 116, helping to keep the connector 100 in place and prevent "flopping" while still allowing free movement when intended by the user. By way of further example, the low-profile geometry of the wing portion 130 of the connector 100 can allow the connector to be used in surgical areas where space is limited (e.g., in the cervical area of the spine). In an exemplary method, the wing portion 130 of the connector 100 can be hooked onto a first rod R1 at a location between two bone anchors to which the rod is coupled, the two bone anchors being implanted in adjacent vertebral levels of the cervical spine. As yet another example, the connector 100 can facilitate independent locking of the first and second rods R1, R2. This can allow the connector 100 to be locked to the first rod R1 to limit or prevent movement of the connector before the second rod R2 is attached and/or locked.

Figure 2A:
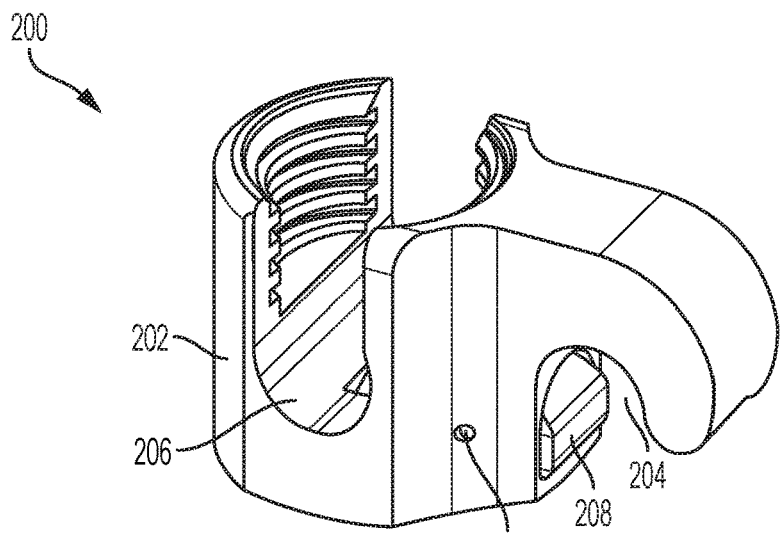
FIG. 2A is a perspective view of a connector.
Figure 2B:
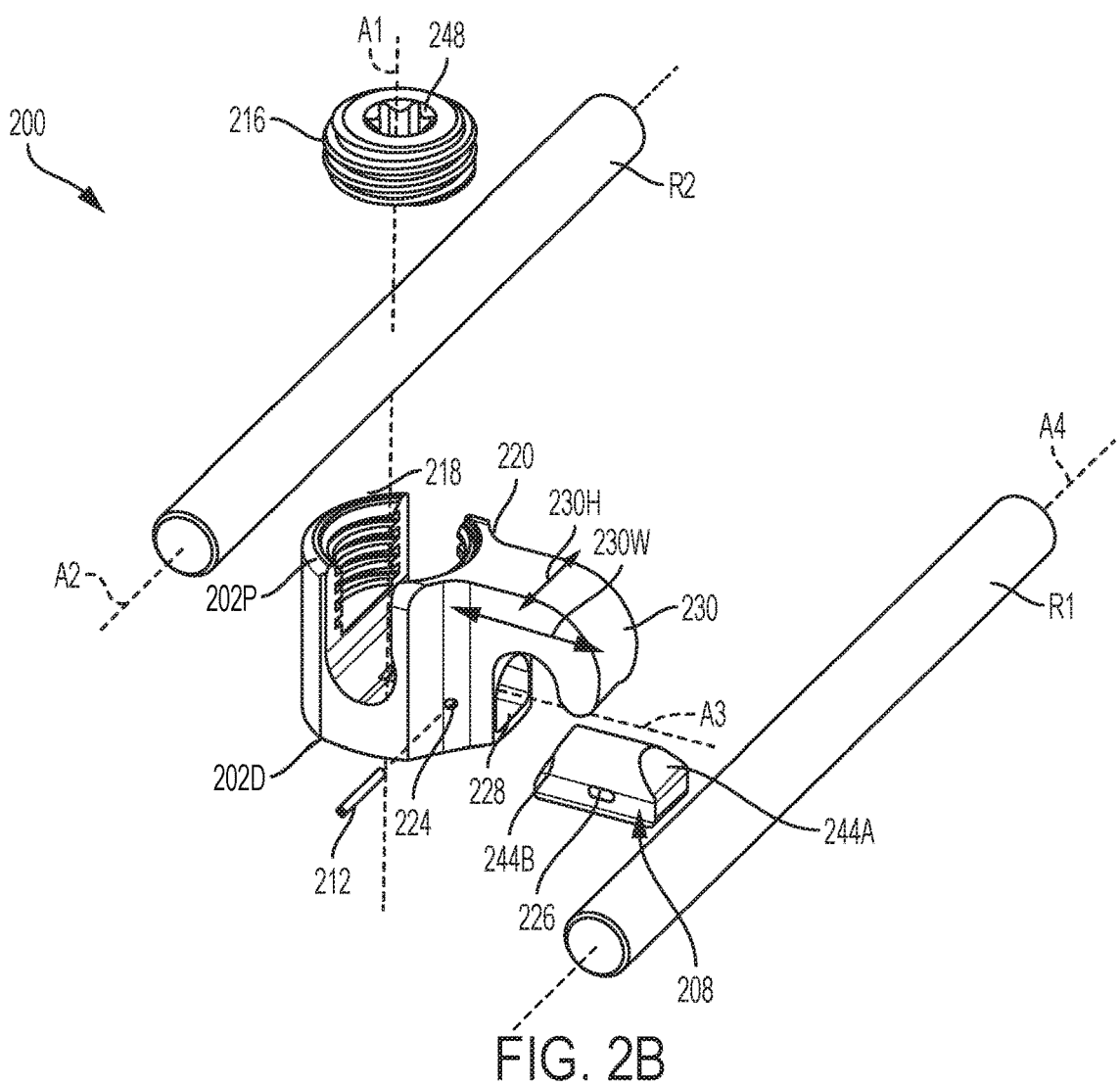
FIG. 2B is an exploded perspective view of the connector of FIG. 2A shown with first and second spinal rods.
Figure 2C:
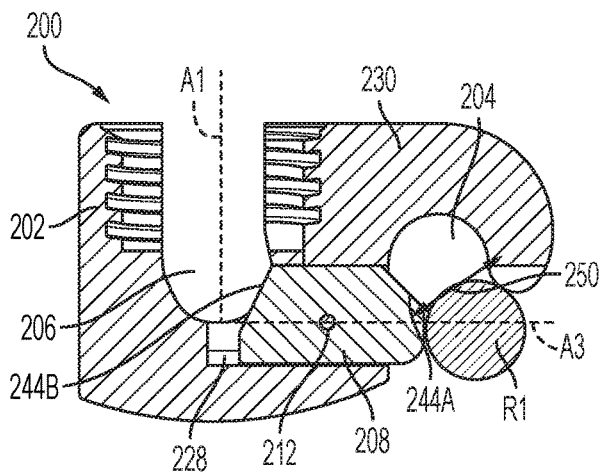
FIG. 2C is a sectional side view of the connector of FIG. 2A in a first configuration.
Figure 2D:
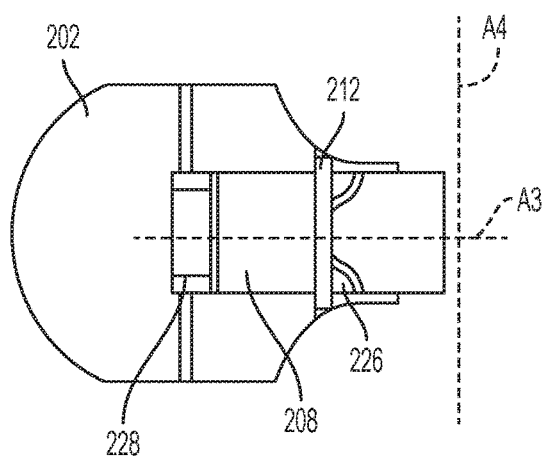
FIG. 2D is a sectional top view of the connector of FIG. 2A in the first configuration.
Figure 2E:
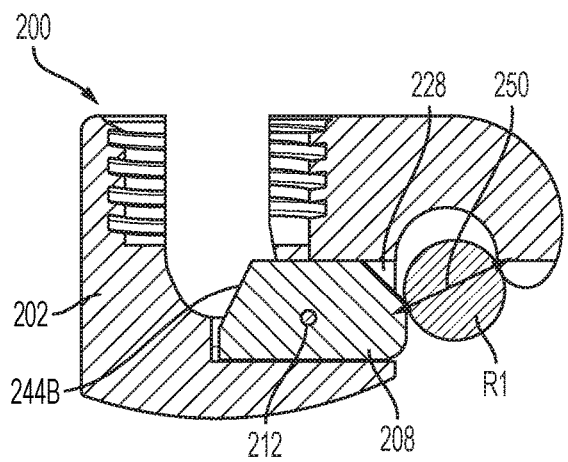
FIG. 2E is a sectional side view of the connector of FIG. 2A in a second configuration.
Figure 2F:
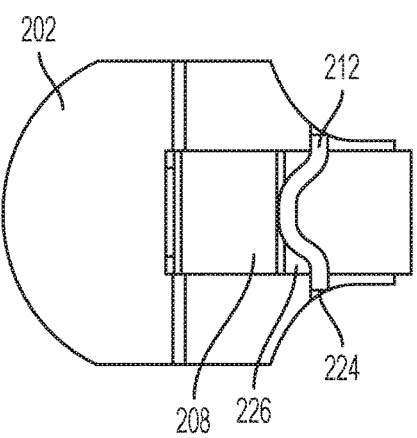
FIG. 2F is a sectional top view of the connector of FIG. 2A in the second configuration.
Figure 2G:
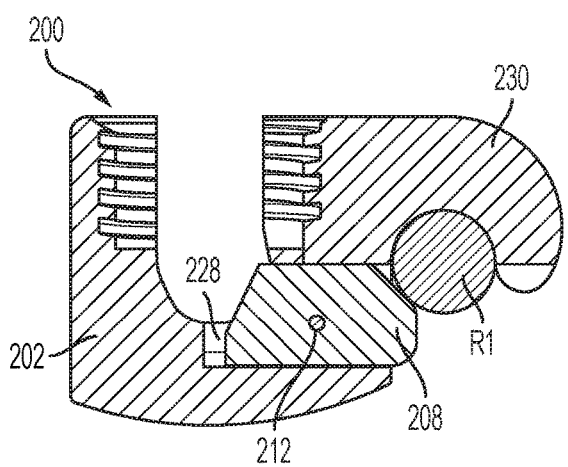
FIG. 2G is a sectional side view of the connector of FIG. 2A in a third configuration.
Figure 2H:
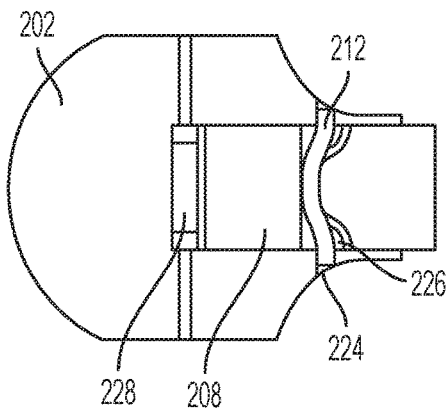
FIG. 2H is a sectional top view of the connector of FIG. 2A in the third configuration.
Figure 21:
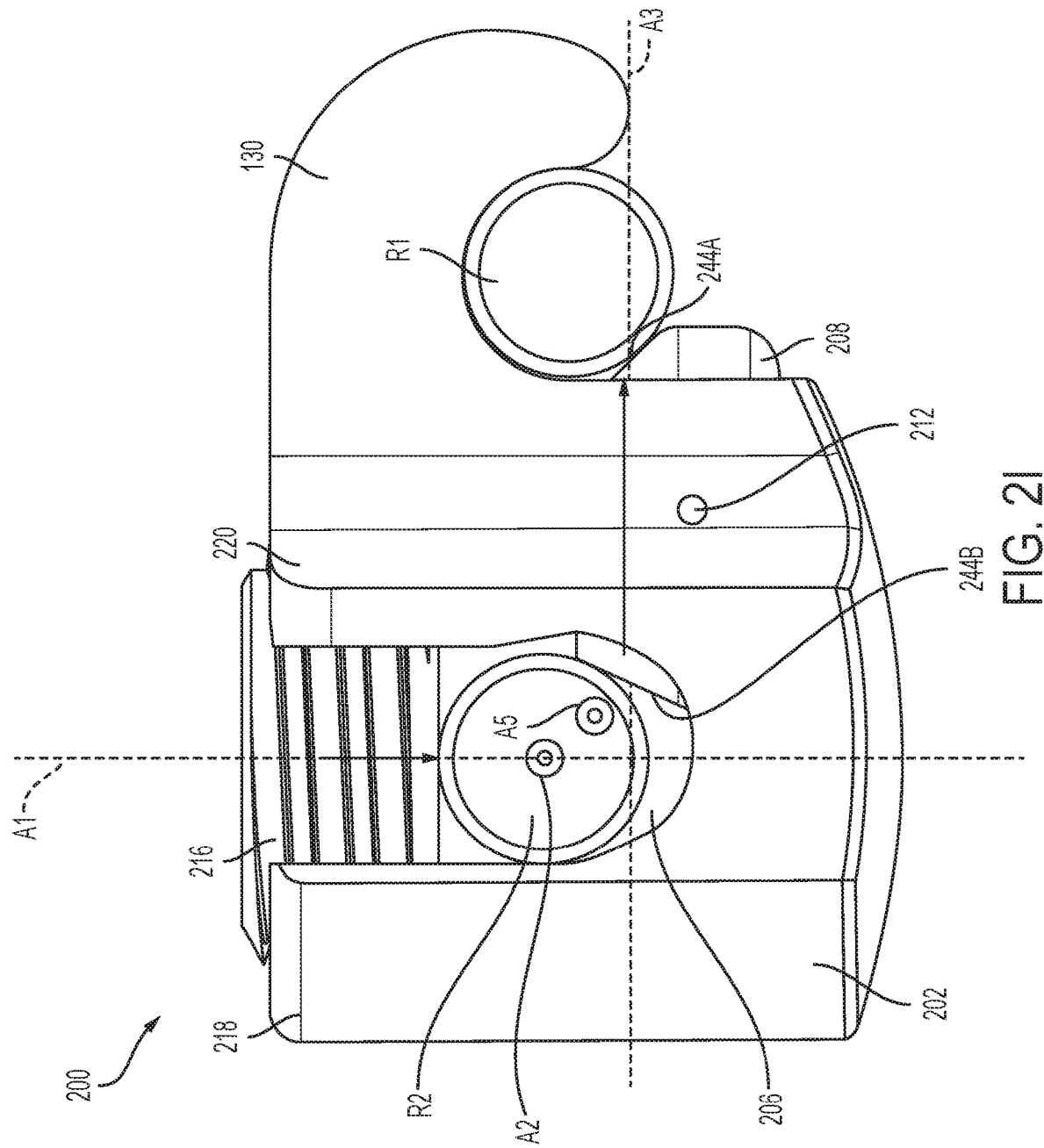
Figure 2J:
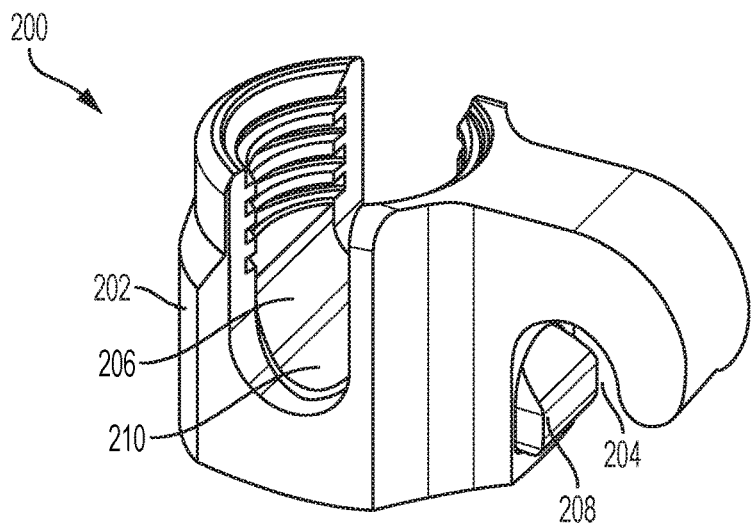
FIG. 2J is a perspective view of the connector of FIG. 2A shown with a saddle.
Figure 2K:
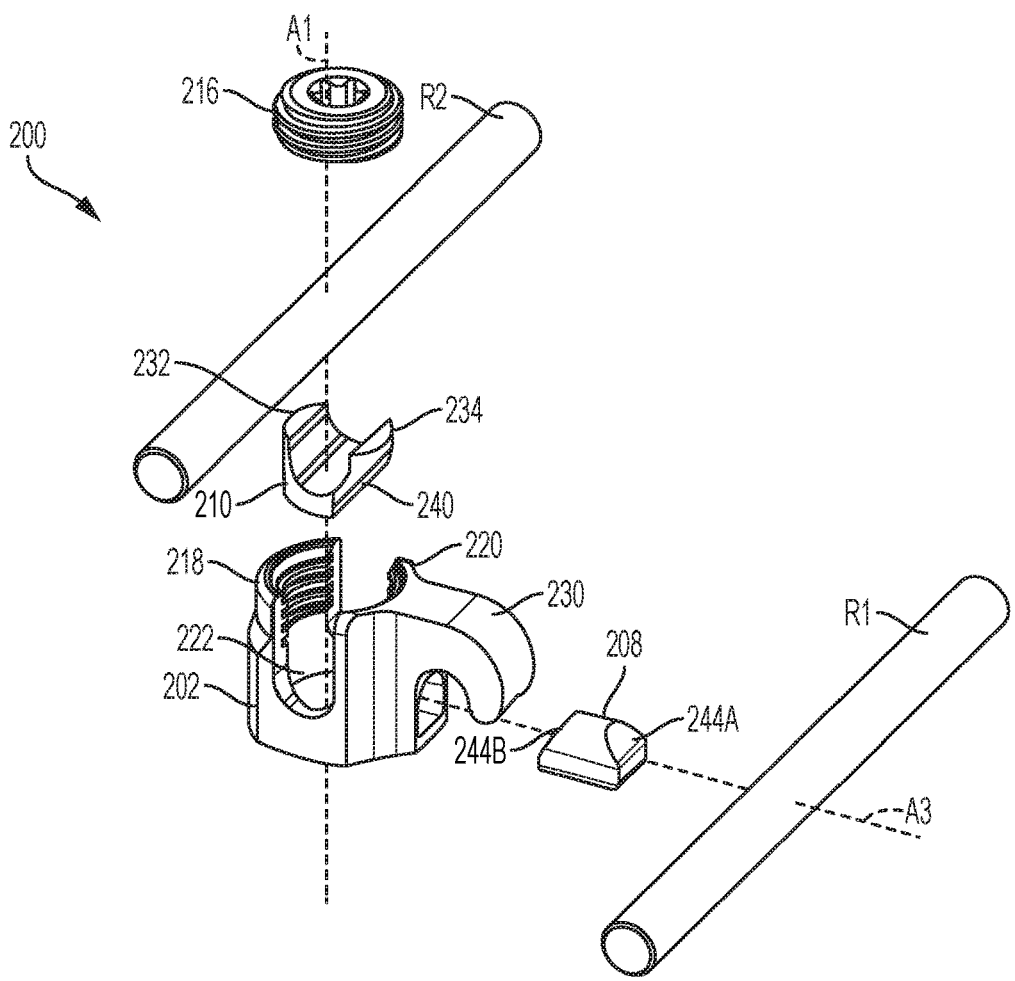
FIG. 2K is an exploded perspective view of the connector and saddle of FIG. 2J shown with first and second spinal rods.
Figure 2L:
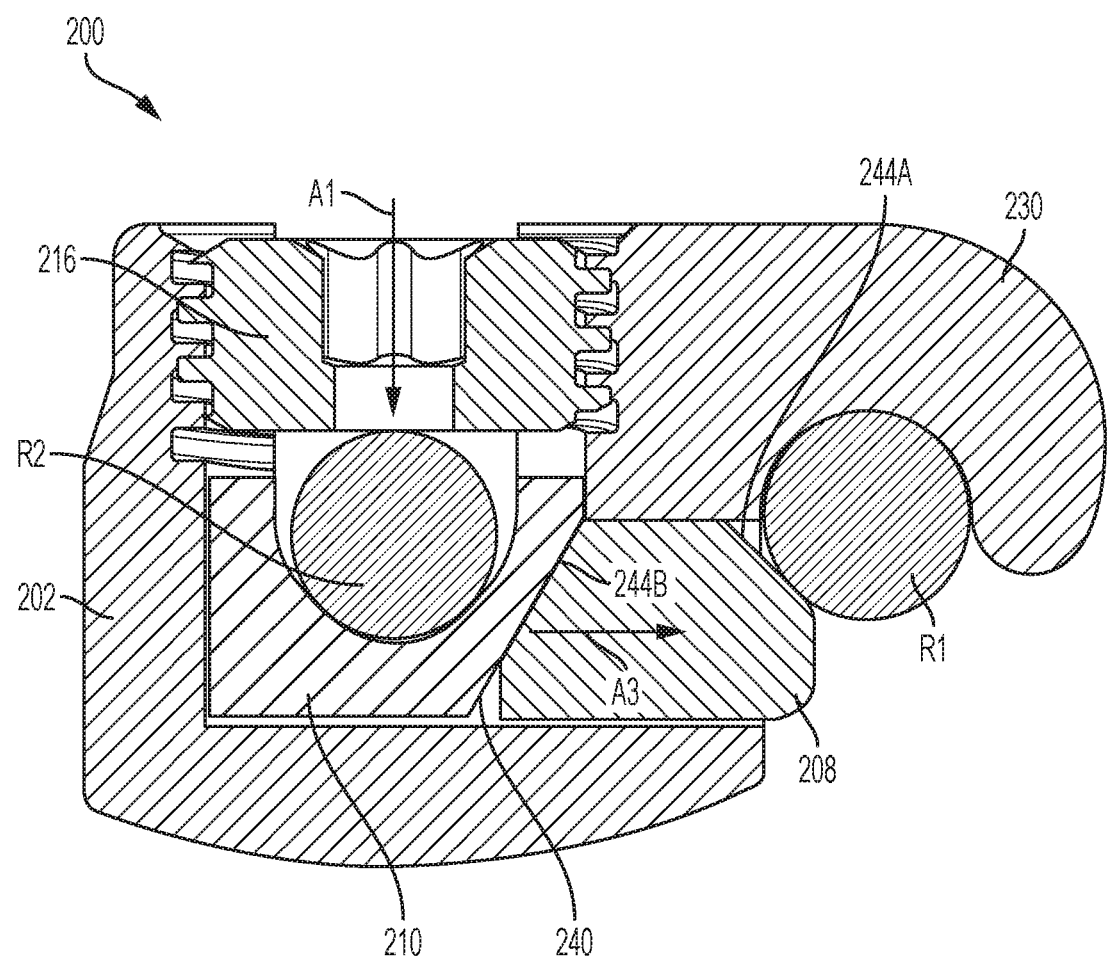
FIG. 2L is a sectional side view of the connector and saddle of FIG. 2J coupled to first and second spinal rods.
Figure 2M:
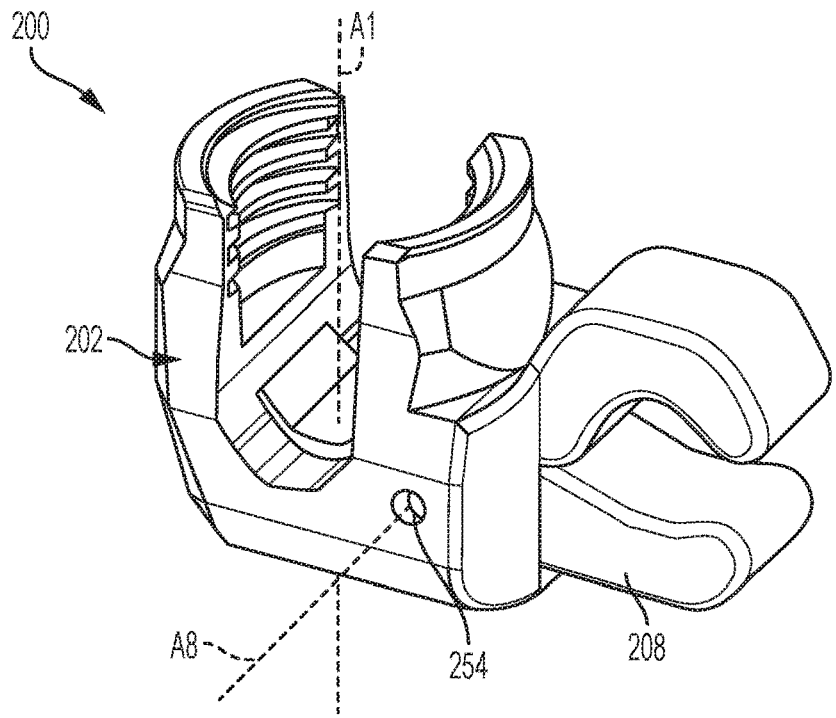
FIG. 2M is a perspective view of the connector of FIG. 2A shown with a pivoting rod pusher.
Figure 2N:
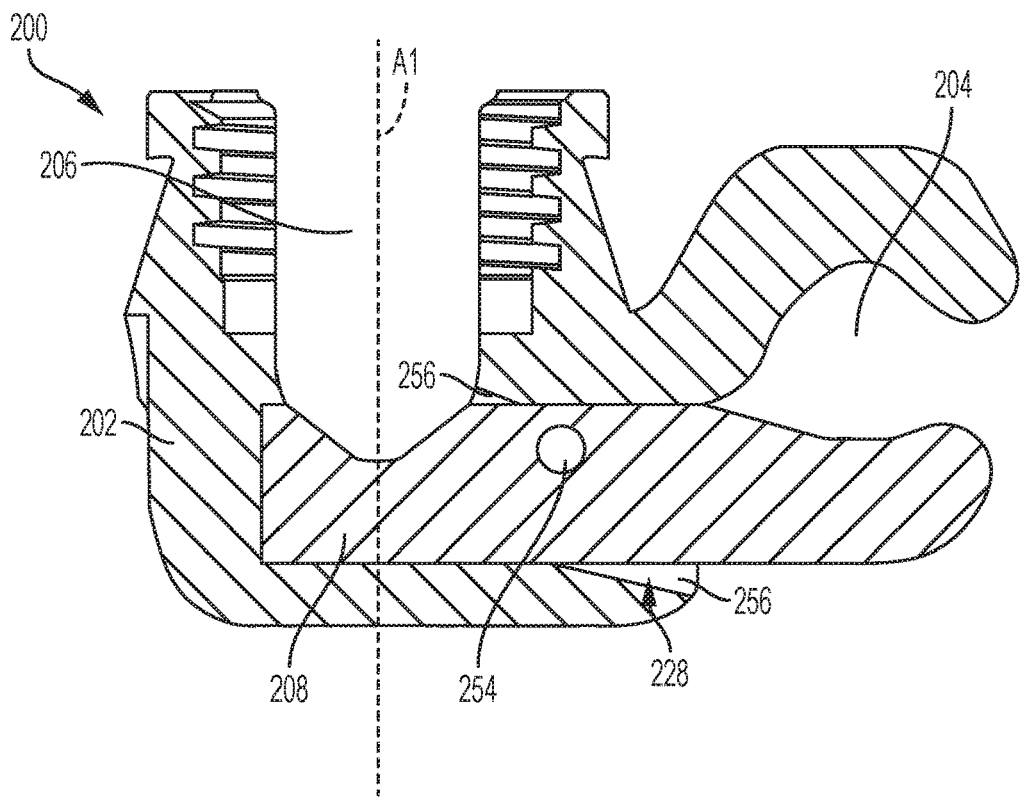
FIG. 2N is a sectional side view of the connector of FIG. 2M.

FIGS. 2A-2N illustrate an exemplary embodiment of a connector 200. As shown, the connector 200 can include a body 202 that defines first and second rod-receiving recesses 204, 206, a rod pusher 208, a bias element or spring wire 212, and a locking element or set screw 216. The rod pusher 208 can be configured to translate laterally within the body 202, and can be biased by the spring wire 212 in a direction that urges the rod pusher into a first rod R1 disposed in the first rod-receiving recess 204. The set screw 216 can be tightened to lock the connector 200 to both the first rod R1 and to a second rod R2 disposed in the second rod-receiving recess 206. The illustrated connector 200 can thus allow for one-step locking of first and second rods R1, R2 to the connector. The connector 200 can include one or more low-profile portions to facilitate use in tight spaces. For example, the first rod-receiving recess 204 can be formed in a portion of the connector body 202 having a reduced-profile, e.g., to fit between bone anchors implanted in adjacent levels of the cervical spine.

The body 202 can include proximal and distal ends 202p, 202d that define a proximal-distal axis A1. The proximal end 202p of the body 202 can include a pair of spaced apart arms 218, 220 that define the second rod-receiving recess 206 therebetween. A rod R2 disposed in the second rod-receiving recess 206 can have a central longitudinal rod axis A2. The second rod-receiving recess 206 can be open in a proximal direction, such that a rod R2 can be inserted into the recess by moving the rod distally with respect to the connector 200. Each of the arms 218, 220 can extend from the distal portion 202d of the body 202 to a free end. The outer surfaces of each of the arms 218, 220 can include a feature (not shown), such as a recess, dimple, notch, projection, or the like, to facilitate coupling of the connector 200 to various instruments. For example, the outer surface of each arm 218, 220 can include an arcuate groove at the respective free end of the arms for attaching the connector 200 to an extension tower or retractor. The arms 218, 220 can include or can be coupled to extension or reduction tabs (not shown) that extend proximally from the body 202 to functionally extend the length of the arms 218, 220. The extension tabs can facilitate insertion and reduction of a rod or other implant, as well as insertion and locking of the set screw 216. The extension tabs can be configured to break away or otherwise be separated from the arms 218, 220. The inner surfaces of each of the arms 218, 220 can be configured to mate with the set screw 216. For example, the inner surfaces of the arms 218, 220 can include threads that correspond to external threads formed on the set screw 216. Accordingly, rotation of the set screw 216 with respect to the body 202 about the axis A1 can be effective to translate the set screw with respect to the body axially along the axis A1.

The distal end 202d of the body 202 can define a tunnel 228 in which the rod pusher 208 can be disposed. The tunnel 228 can extend along a rod pusher axis A3 between the second rod-receiving recess 206 and the first rod-receiving recess 204. The rod pusher 208 can be configured to translate within the tunnel 228 along the axis A3. The axis A3 can be perpendicular or substantially perpendicular to the axis A1. The axis A3 can also be perpendicular or substantially perpendicular to the axis A2. The tunnel 228 can have a shape that is substantially a negative of the exterior shape of the rod pusher 208. A through-bore 224 can be formed in the body 202 such that the through-bore intersects with the tunnel 228. The through-bore 224 can extend perpendicular or substantially perpendicular to the axis A3. The through-bore 224 can be sized to receive the spring wire 212 therein, as described further below. The through-bore 224 can be open at both ends or one or both ends can be closed.

The body 202 can include a cantilevered wing portion 230 that defines the first rod-receiving recess 204. A rod R1 disposed in the first rod-receiving recess 204 can have a central longitudinal rod axis A4. The axis A4 can be parallel to the axis A2 as shown, or can be perpendicular or obliquely angled with respect to the axis A2. The wing portion 230 can extend radially-outward from the second arm 220 of the body 202. The wing portion 230 can have a width 230W and a height 230H. A ratio of the width 230W to the diameter of the first rod-receiving recess 204 (or of a rod R1 disposed therein) can be less than about 1.5:1, less than about 2:1, and/or less than about 3:1. A ratio of the height 230H to the diameter of the first rod-receiving recess 204 (or of a rod R1 disposed therein) can be less than about 0.5:1, less than about 1:1, and/or less than about 2:1. In some embodiments, the height 230H can be less than about 5 mm, less than about 4 mm, and/or less than about 3 mm. The first rod-receiving recess 204 can be open in a distal direction such that a rod R1 can be inserted into the recess by moving the connector 200 distally with respect to the rod. In other embodiments, the first rod-receiving recess 204 can be open in a proximal direction, e.g., by flipping the wing portion 230 and forming it such that it extends from a distal portion of the body 202, or in a lateral direction.

As noted above, the rod pusher 208 can be slidably disposed within the tunnel 228 of the body 202 and can be configured to translate with respect to the body along the axis A3. The rod pusher 208 can include a first bearing surface 244A configured to contact and bear against a first rod R1 disposed in the first rod-receiving recess 204. The bearing surface 244A can extend at an oblique angle with respect to a longitudinal axis of the rod pusher 208 such that the bearing surface is ramped. The bearing surface 244A can be planar as shown, or can be convex, concave, pointed, sharpened, etc. For example, the bearing surface 244A can be concave and can define a section of a cylinder, such that the bearing surface matches or approximates the contour of a cylindrical rod R1 disposed in the first rod-receiving recess 204. The rod pusher 208 can include a second bearing surface 244B configured to contact and bear against a second rod R2 disposed in the second rod-receiving recess 206. The bearing surface 244B can extend at an oblique angle with respect to a longitudinal axis of the rod pusher 208 such that the bearing surface is ramped. The bearing surface 244B can be planar as shown, or can be convex, concave, pointed, sharpened, etc. For example, the bearing surface 244B can be concave and can define a section of a cylinder, such that the bearing surface matches or approximates the contour of a cylindrical rod R2 disposed in the second rod-receiving recess 206.

The rod pusher 208 can include a through bore 226. The through-bore 226 can extend perpendicular or substantially perpendicular to the axis A3. The through-bore 226 can be sized to receive the spring wire 212 therein. In at least some positions of the rod pusher 208 with respect to the body 202, the through-bore 226 of the rod pusher can be aligned with the through-bore 224 of the body, such that the spring wire 212 extends through both through-bores 224, 226. As best shown in FIGS. 2D, 2F, and 2H, the through-bore 226 can include a middle portion and opposed end portions. The middle portion of the through-bore 226 can approximate the dimensions of the spring wire 212. For example, the middle portion can be cylindrical and can have a diameter that is substantially equal to the diameter of the spring wire 212. The end portions of the through-bore 226 can be elongated or can otherwise have a dimension greater than the diameter of the spring wire 212 to allow the rod pusher 208 to translate along the axis A3 and to accommodate the bend radius of the spring wire 212 during such translation.

The bias element can be configured to bias the rod pusher 208 towards the first rod-receiving recess 204. In the illustrated embodiment, the bias element is a cylindrical spring wire 212. The spring wire 212 can be formed from a resilient material such that, when deformed from a straight line, the spring wire tends to flex back towards its straight resting configuration. Accordingly, when deformed by movement of the rod pusher 208, the spring wire 212 can exert a force against the interior of the through-bore 226 to urge the rod pusher 208 towards the first rod-receiving recess 204. While a straight, cylindrical spring wire 212 is shown, various other bias elements can be used instead or in addition, such as non-straight or non-cylindrical wires, leaf springs, spring clips, wave springs, coil springs, and the like. In some embodiments, the bias element can be omitted. For example, the rod pusher 208 can be free to float within the tunnel 228, or can be retained by a pin or other retention feature without being biased towards the first rod-receiving recess 204.

The set screw 216 can include an exterior thread configured to mate with the interior threads formed on the arms 218, 220 of the body 202 to allow the set screw to be advanced or retracted along the axis A1 with respect to the body by rotating the set screw about the axis A1. The set screw 216 can include a driving interface 248 configured to receive a driver for applying a rotational force to the set screw about the axis A1. The distal surface of the set screw 216 can be configured to contact and bear against a rod R2 disposed in the second rod-receiving 206 recess to lock the rod to the connector 200. When tightened against the rod R2, the set screw 216 can prevent the rod from translating relative to the connector 200 along the axis A2 and/or from rotating with respect to the connector about the axis A2. While a set screw 216 is shown, it will be appreciated that other locking elements can be used instead or addition, such as a closure cap that advances and locks by quarter-turn rotation, a closure cap that slides in laterally without rotating, a nut that threads onto an exterior of the connector 200, and so forth.

Operation of the connector 200 is illustrated schematically in FIGS. 2C-2H.

As shown in FIGS. 2C-2D, the connector 200 can have a resting configuration in which no rod is disposed in the first or second rod-receiving recesses 204, 206. In this configuration, the biasing force of the spring wire 212 can cause the rod pusher 208 to slide towards the first rod-receiving recess 204.

In the resting configuration, the wing portion 230 of the body 202 and the free end of the rod pusher 208 can define an aperture 250 that is smaller than the diameter of a first rod R1 to which the connector 200 is to be coupled. Accordingly, as shown in FIGS. 2E-2F, as the rod R1 is inserted into the first rod-receiving recess 204, the rod bears against the rod pusher 208 to move the connector 200 out of the resting configuration. Insertion of the rod R1 can move the rod pusher 208 along the axis A3, thereby deforming the spring wire 212 from its resting state. As the largest cross-sectional portion of the rod R1 is positioned in the aperture 250, the rod pusher 208 can be displaced to its furthest distance from the first rod-receiving recess 204.

As shown in FIGS. 2G-2H, once the largest cross-sectional portion of the rod R1 clears the aperture 250 as the rod is seated in the first rod-receiving recess 204, the biasing force of the spring wire 212 can cause the rod pusher 208 to move back along the axis A3 towards the first rod-receiving recess. This movement can at least partially close the aperture 250 around the rod R1 to capture the rod in the first rod-receiving recess 204. The biasing force of the spring wire 212 can resist retrograde movement of the rod pusher 208 and thus resist disconnection of the connector 200 from the first rod R1. The geometry of the connector 200 can be selected such that, when the rod R1 is fully seated in the first rod-receiving recess 204, the spring wire 212 is deformed from its resting state. The spring wire 212 can thus press the rod pusher 208 against the rod R1 to provide a friction or drag effect, before the set screw 216 is tightened and/or before a second rod R2 is positioned in the connector 200.

A second rod R2 can be positioned in the second rod-receiving recess 206, and the set screw 216 can be tightened to lock the connector 200 to the first and second rods R1, R2. As the set screw 216 is tightened, the second rod R2 can press against the second bearing surface 244B of the rod pusher 208, urging the rod pusher towards the first rod-receiving recess 204 and firmly into contact with the rod R1. When the set screw 216 is tightened, the connector 200 can be locked to the first and second rods R1, R2 to resist or prevent translation of the rods R1, R2 with respect to the connector along the axes A2, A4 and to resist or prevent rotation of the rods R1, R2 with respect to the connector about the axes A2, A4.

As shown in FIG. 2I, the second rod-receiving recess 206 can be shaped to encourage contact between the second rod R2 and the second bearing surface 244B of the rod pusher 208. In other words, the recess 206 can be shaped to reduce or eliminate the risk that the second rod R2 will only bear against the floor of the recess 206 when the set screw 216 is tightened, without applying sufficient force to the bearing surface 244B. As shown, the recess 206 can include a relief disposed in alignment with the end of the tunnel 228 such that the rod pusher 208 protrudes into the recess. The recess 206 can thus be asymmetrical about the axis A1, and can deviate from a symmetrical U-shape. When the rod R2 is bottomed out in the recess 206, the central longitudinal axis A2 of the rod can be offset from the axis A1. The central longitudinal axis of the rod R2 when the rod is fully seated is shown in FIG. 2I as axis A5. The recess 206 can be configured such that, as the rod R2 is seated within the recess 206, it translates distally along the axis A1 and laterally along the axis A3.

As shown in FIGS. 2J-2L, the connector 200 can include a saddle 210. The saddle 210 can be included in addition to the asymmetrical recess 206 or as an alternative thereto. The saddle 210 can be positioned within a cavity 222 formed in the body 202. The saddle 210 can be generally cylindrical with first and second arms 232, 234 extending in a proximal direction to respective free ends of the arms. The first and second arms 232, 234 can be aligned with the first and second arms 218, 220 of the body 202 such that a recess defined therebetween is aligned with the second rod-receiving recess 206. Accordingly, the second rod R2 can be simultaneously cradled between the arms 232, 234 of the saddle 210 and the arms 218, 220 of the body 202 when the rod is disposed in the second rod-receiving recess 206. The saddle 210 can include a ramped bearing surface 240 configured to contact and bear against the second bearing surface 244B of the rod pusher 208. The bearing surface 240 can extend at an oblique angle with respect to the axis A1. The bearing surface 240 can be planar as shown, or can be convex, concave, pointed, sharpened, etc. In operation, a force applied to the saddle 210 along the direction A1, e.g., by tightening the set screw 216 down onto the saddle or down onto a rod R2 disposed in the saddle, can cause the saddle 210 to translate distally with respect to the body 202 and cause the bearing surface 240 to ramp along the bearing surface 244B of the rod pusher 208, urging the rod pusher towards the first rod-receiving recess 204 along the axis A3. Accordingly, tightening the set screw 216 can be effective to simultaneously lock both rods R1, R2 to the connector 200. The saddle 210 can allow for locking of rods having different diameters in the second rod-receiving recess 206, while still ensuring that, regardless of the diameter of the second rod R2, sufficient force is applied to the rod pusher 208 to lock the first rod R1.

As shown in FIGS. 2M-2N, the rod pusher 208 can be configured to pivot with respect to the body 202, instead of translating relative to the body or in addition to translating relative to the body. The tunnel 228 can be oversized or can include one or more reliefs 256 formed therein to allow the rod pusher 208 to rotate within the tunnel about a pivot axis A8. The rod pusher 208 can be pivotally mounted within the tunnel 228 by a pivot pin 254. The connector 200 can include a bias element to bias the rod pusher 208. For example, a spring wire of the type described above can be used to bias translation of the rod pusher 208 relative to the body 202. By way of further example, the pivot pin 254 can be a torsion bar that biases rotation of the rod pusher 208 relative to the body 202. Other ways of biasing rotation of the rod pusher 208 can be used instead or in addition, such as coil springs, leaf springs, and the like. In operation, a force applied to a first end of the rod pusher 208 along the direction A1, e.g., by tightening the set screw 216 down onto a rod R2 disposed in the second recess 206, can cause the rod pusher to pivot or rotate about the pivot axis A8, urging a second opposite end of the rod pusher against a rod R1 disposed in the first recess 204. Accordingly, tightening the set screw 216 can be effective to simultaneously lock both rods R1, R2 to the connector 200. The connector of FIGS. 2M-2N can provide a mechanical advantage in locking the first rod R1 due to the lever action of the pivoting rod pusher 208.

In some embodiments, the arms 232, 234 can extend proximally past the maximum dimension of the rod R2 and the set screw 216 can include an outer screw configured to bear against a proximal-facing surface of the arms. An inner set screw can be threadably mounted within the outer set screw. Accordingly, the outer set screw can be tightened first to press down on the saddle 210 and lock the first rod R1 in the first rod-receiving recess 204. Then, the inner set screw can be tightened to press down on the second rod R2 and lock the second rod in the second rod-receiving recess 206. The dual set screw can thus facilitate independent locking of the first and second rods R1, R2 to the connector 200. While not shown in FIGS. 2J-2L, embodiments of the connector 200 that include a saddle 210 can also include a bias element as described above for biasing the rod pusher 208 towards the first rod-receiving recess 204.

The connector 200 can thus be used to connect a first spinal rod R1 to a second spinal rod R2. While use of the connector 200 with first and second spinal rods is generally described herein, it will be appreciated that the connector can instead be configured for use with other types of orthopedic hardware, whether implanted or external. For example, one or both halves of the connector 200 can be modified to couple other various components to each other (e.g., to couple a rod to a plate, to couple a plate to a plate, to couple a rod to cable, to couple a cable to a cable, and so forth).

The connector 200 can provide various benefits for the user and/or patient. For example, the biased rod pusher 208 can provide tactile feedback when the connector 200 is "snapped" onto the first rod R1, giving the user confidence that the rod has been attached successfully before tightening the connector. The biased rod pusher 208 can also apply friction or "drag" to the rod R1 prior to locking the set screw 216, helping to keep the connector in place and prevent "flopping" while still allowing free movement when intended by the user. By way of further example, the low-profile geometry of the wing portion 230 of the connector 200 can allow the connector to be used in surgical areas where space is limited (e.g., in the cervical area of the spine). In an exemplary method, the wing portion 230 of the connector 200 can be hooked onto a first rod R1 at a location between two bone anchors to which the rod is coupled, the two bone anchors being implanted in adjacent vertebral levels of the cervical spine. As yet another example, the connector 200 can facilitate simultaneous and/or single-step locking of the first and second rods R1, R2. This can allow the connector 200 to be locked to both rods R1, R2 with minimal steps. In other embodiments, the connector 200 can facilitate independent locking of the rods R1, R2, e.g., with use of a saddle 210 and dual set screw.

FIGS. 3A-3H illustrate an exemplary embodiment of a connector 300. As shown, the connector 300 can include a body 302 that defines first and second rod-receiving recesses 304, 306, a rod pusher 308, a bias element or leaf spring 312, a first locking element or set screw 314, and a second locking element or set screw 316. The rod pusher 308 can be biased by the leaf spring 312 in a direction that urges the rod pusher into a first rod R1 disposed in the first rod-receiving recess 304. The first set screw 314 can be tightened to lock the connector 300 to the first rod R1. The second set screw 316 can be tightened to lock a second rod R2 in the second rod-receiving recess 306 of the connector 300. The illustrated connector 300 can thus allow for independent locking of first and second rods R1, R2 to the connector. The connector 300 can include one or more low-profile portions to facilitate use in tight spaces. For example, the first rod-receiving recess 304 can be formed in a portion of the connector body 302 having a reduced-profile, e.g., to fit between bone anchors implanted in adjacent levels of the cervical spine.

The body 302 can include proximal and distal ends 302p, 302d that define a proximal-distal axis A1. The proximal end 302p of the body 302 can include a pair of spaced apart arms 318, 320 that define the second rod-receiving recess 306 therebetween. A rod R2 disposed in the second rod-receiving recess 306 can have a central longitudinal rod axis A2. The second rod-receiving recess 306 can be open in a proximal direction, such that a rod R2 can be inserted into the recess by moving the rod distally with respect to the connector 300. Each of the arms 318, 320 can extend from the distal portion 302d of the body 302 to a free end. The outer surfaces of each of the arms 318, 320 can include a feature (not shown), such as a recess, dimple, notch, projection, or the like, to facilitate coupling of the connector 300 to various instruments. For example, the outer surface of each arm 318, 320 can include an arcuate groove at the respective free end of the arms for attaching the connector 300 to an extension tower or retractor. The arms 318, 320 can include or can be coupled to extension or reduction tabs (not shown) that extend proximally from the body 302 to functionally extend the length of the arms 318, 320. The extension tabs can facilitate insertion and reduction of a rod or other implant, as well as insertion and locking of the set screw 316. The extension tabs can be configured to break away or otherwise be separated from the arms 318, 320. The inner surfaces of each of the arms 318, 320 can be configured to mate with the second set screw 316. For example, the inner surfaces of the arms 318, 320 can include threads that correspond to external threads formed on the second set screw 316. Accordingly, rotation of the second set screw 316 with respect to the body 302 about the axis A1 can be effective to translate the set screw with respect to the body axially along the axis A1.

The body 302 can include a cantilevered wing portion 330 that defines the first rod-receiving recess 304. A rod R1 disposed in the first rod-receiving recess 304 can have a central longitudinal rod axis A4. The axis A4 can be parallel to the axis A2 as shown, or can be perpendicular or obliquely angled with respect to the axis A2. The wing portion 330 can extend radially-outward from the second arm 320 of the body 302. The wing portion 330 can have a width 330W and a height 330H. A ratio of the width 330W to the diameter of the first rod-receiving recess 304 (or of a rod R1 disposed therein) can be less than about 1.5:1, less than about 2:1, and/or less than about 3:1. A ratio of the height 330H to the diameter of the first rod-receiving recess 304 (or of a rod R1 disposed therein) can be less than about 0.5:1, less than about 1:1, and/or less than about 2:1. In some embodiments, the height 330H can be less than about 5 mm, less than about 4 mm, and/or less than about 3 mm. The first rod-receiving recess 304 can be open in a lateral direction such that a rod R1 can be inserted into the recess by moving the connector 300 laterally with respect to the rod. In other embodiments, the first rod-receiving recess 304 can be open in a proximal or distal direction, e.g., by flipping the orientation of the wing portion 330, the first set screw 314, and the rod pusher 308.

A tunnel 328 can be formed in the body 302 and can extend along a tunnel axis A6 between a proximal-facing surface of the body 302 and the first rod-receiving recess 304. The tunnel 328 can be formed in the wing portion 330 of the body 302. The tunnel 328 can have a shape that is substantially a negative of the exterior shape of the rod pusher 308. The rod pusher 308 can be slidably disposed within the tunnel 328 such that the rod pusher can translate along the axis A6 with respect to the body 302. A through-bore 324 can be formed in the body 302 such that the through-bore intersects with the tunnel 328. The through-bore 324 can extend perpendicular or substantially perpendicular to the axis A6. The through-bore 324 can be sized to receive the leaf spring 312 therein, as described further below. The through-bore 324 can be rectangular or substantially rectangular as shown, or can have other shapes. The through-bore 324 can have a maximum height in the proximal-distal direction that is less than a corresponding height of the leaf spring 312 in its resting position. Accordingly, when disposed within the through-bore 324, the leaf spring 312 can be maintained in a deformed position such that it exerts a constant biasing force on the rod pusher 308. The through-bore 324 can be open at both ends or one or both ends can be closed.

A proximal end of the tunnel 328 can define a recess 326 sized to receive at least a portion of the first set screw 314. The inner surface of the recess 326 can be configured to mate with the first set screw 314. For example, the inner surface 326 can include threads that correspond to external threads formed on the first set screw 314. Accordingly, rotation of the first set screw 314 with respect to the body 302 about the axis A6 can be effective to translate the set screw with respect to the body axially along the axis A6. The recess 326 can be cylindrical as shown or can be conical or have other shapes.

As noted above, the rod pusher 308 can be slidably disposed within the tunnel 328 of the body 302 and can be configured to translate with respect to the body along the axis A6. The rod pusher 308 can include a bearing surface 344 configured to contact and bear against a rod R1 disposed in the first rod-receiving recess 304. The bearing surface 344 can include a distal-facing surface of the rod pusher 308. At least a portion of the bearing surface 344 can extend at an oblique angle with respect to a longitudinal axis of the rod pusher 308 such that the bearing surface is ramped. The bearing surface 344 can be planar as shown, or can be concave, convex, pointed, sharpened, etc. For example, the bearing surface 344 can be concave and can define a section of a cylinder, such that the bearing surface matches or approximates the contour of a cylindrical rod R1 disposed in the first rod-receiving recess 304. The rod pusher 308 can include a projection 338 or other mating feature for mating the rod pusher to the leaf spring 312. The projection 338 can include an undercut or reduced distal portion and an enlarged proximal portion.

The bias element can be configured to bias the rod pusher 308 towards the first rod-receiving recess 304. In the illustrated embodiment, the bias element is a rectangular leaf spring 312. The leaf spring 312 can be formed from a resilient material such that, when deformed from a resting position, the leaf spring 312 tends to flex back towards the resting configuration. Accordingly, when deformed by movement of the rod pusher 308, the leaf spring 312 can exert a force against the interior of the through-bore 326 to urge the rod pusher 308 towards the first rod-receiving recess 304. While a flat rectangular leaf spring 312 is shown, various other bias elements can be used instead or in addition, such as spring wires, spring clips, wave springs, coil springs, and the like. In some embodiments, the bias element can be omitted. For example, the rod pusher 308 can be free to float within the tunnel 328, or can be retained by a pin or other retention feature without being biased towards the first rod-receiving recess 304. The leaf spring 312 can include an opening 336 or other mating feature for mating the leaf spring to the rod pusher 308. In the illustrated embodiment, the leaf spring 312 includes a keyed opening 336 configured to mate with the projection 338 of the rod pusher 308. The opening 336 can have a first portion 336A with a diameter that is large enough for the enlarged proximal portion of the projection 338 to pass through the opening. The opening 336 can have a second portion 336B with a diameter that is large enough for the reduced distal portion of the projection 338 to pass through the opening but not large enough for the enlarged proximal portion of the projection 338 to pass through the opening. The leaf spring 312 can thus be configured to retain the rod pusher 308 within the body 302 and vice versa.

Figure 3A:
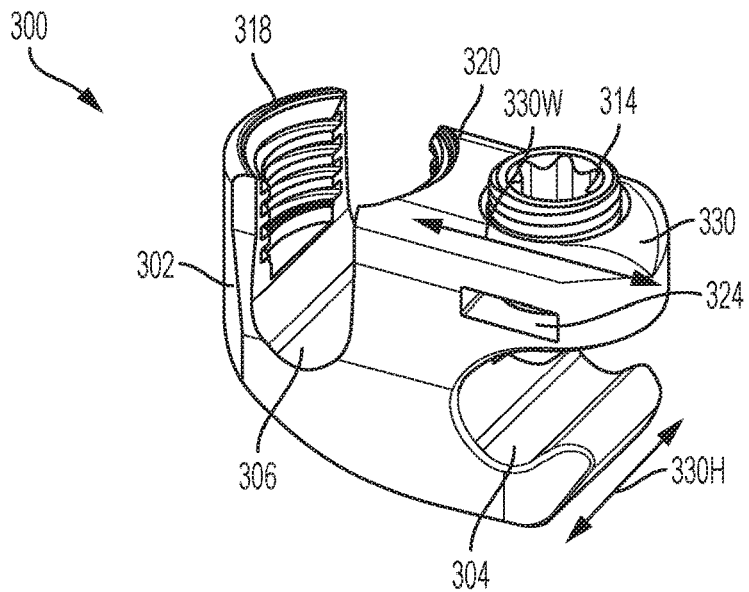
FIG. 3A is a perspective view of a connector.
Figure 3B:
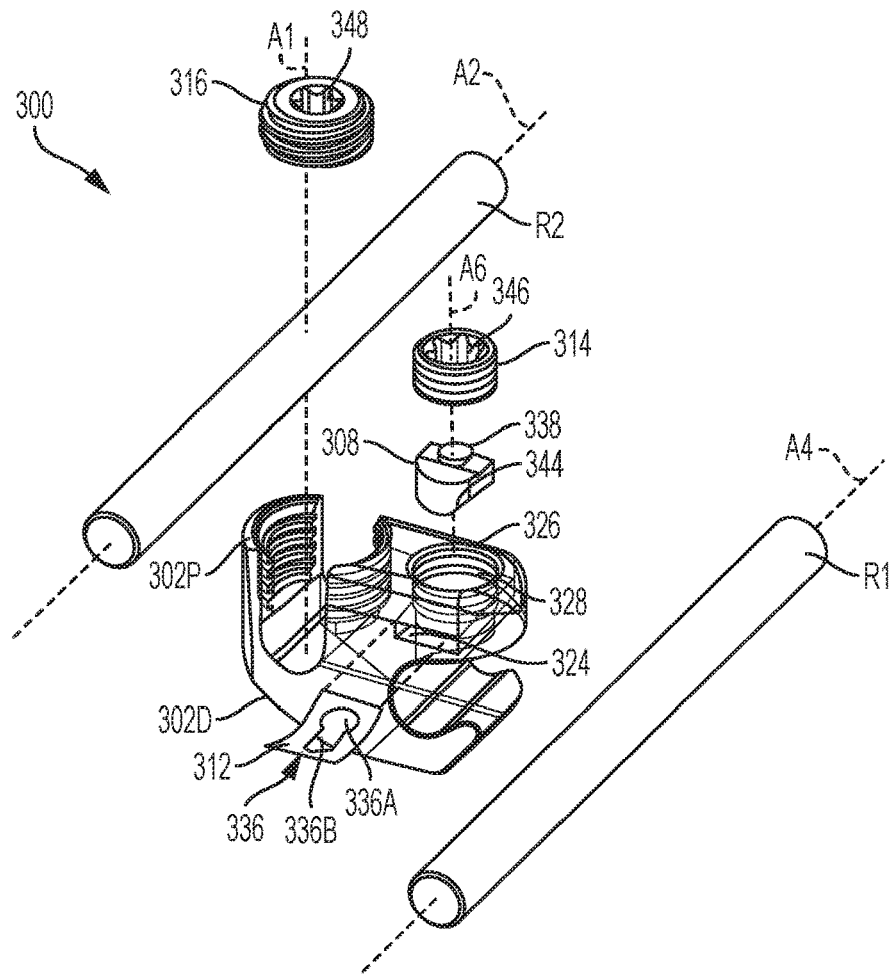
FIG. 3B is an exploded perspective view of the connector of FIG. 3A shown with first and second spinal rods, with a body of the connector shown as transparent.
Figure 3C:
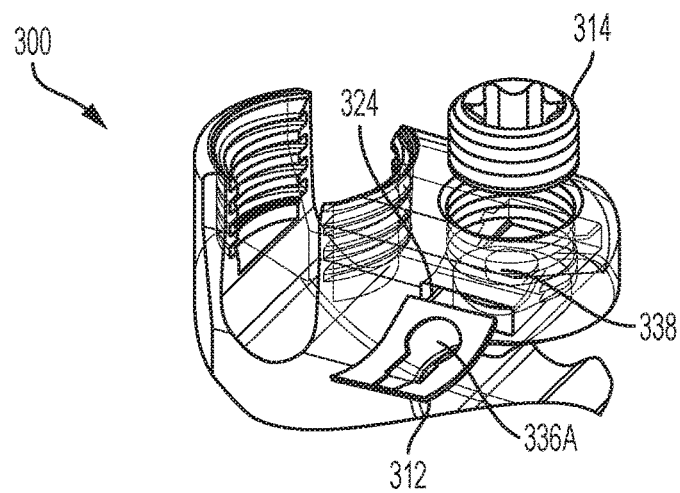
FIG. 3C is a perspective view of the connector of FIG. 3A in a first state of assembly, with a body of the connector shown as transparent.
Figure 3D:
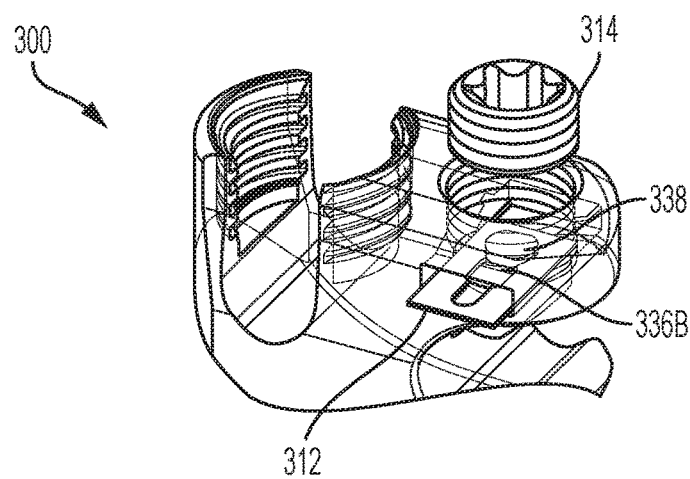
FIG. 3D is a perspective view of the connector of FIG. 3A in a second state of assembly, with a body of the connector shown as transparent.
Figure 3E:
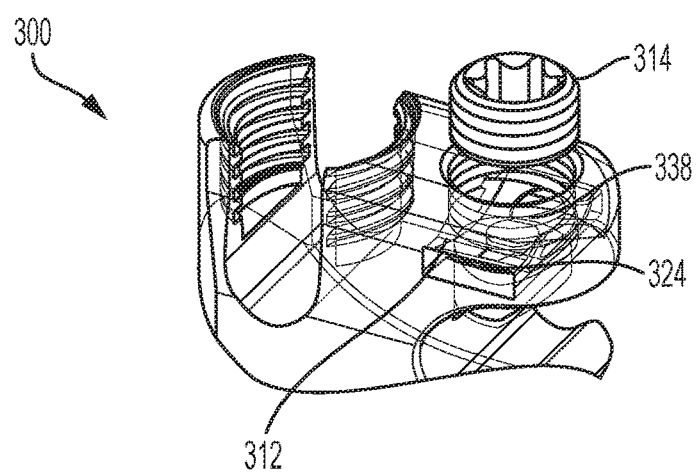
FIG. 3E is a perspective view of the connector of FIG. 3A in a third state of assembly, with a body of the connector shown as transparent.

Assembly of the leaf spring 312 to the rod pusher 308 is illustrated schematically in FIGS. 3C-3E. As shown in FIG. 3C, the rod pusher 308 can be inserted into the tunnel 328 and positioned distal to the through-bore 324. The leaf spring 312 can be inserted into the through-bore 324 to position the first portion 336A of the opening 336 in line with the projection 338 of the rod pusher 308, as shown in FIG. 3D. The rod pusher 308 can be moved proximally to pass the projection 338 through the first portion 336A of the opening 336, and then the leaf spring 312 can be inserted further into the through-bore 324 to position the projection 338 in the second portion 336B of the opening 336, as shown in FIG. 3E. In this position, the enlarged proximal portion of the projection 338 sits proximal to the leaf spring 312 and cannot pass through the opening 336, thereby retaining the rod pusher 308 within the body 302. The spring force of the leaf spring 312 acting against the interior of the through-bore 324 can be effective to retain the leaf spring within the through-bore.

The first set screw 314 can include an exterior thread configured to mate with the interior threads of the recess 326 to allow the first set screw to be advanced or retracted along the axis A6 with respect to the body 302 by rotating the first set screw about the axis A6. The first set screw 314 can include a driving interface 346 configured to receive a driver for applying a rotational force to the first set screw about the axis A6. The distal surface of the first set screw 314 can be configured to contact and bear against a portion of the rod pusher 308, e.g., the projection 338, to urge the rod pusher 308 against a rod R1 disposed in the first rod-receiving 304 recess and lock the rod to the connector 300. When tightened against the rod pusher 308 and, by extension, the rod R1, the first set screw 314 can prevent the rod from translating relative to the connector 300 along the axis A4 and/or from rotating with respect to the connector about the axis A4. While a first set screw 314 is shown, it will be appreciated that other locking elements can be used instead or addition, such as a closure cap that advances and locks by quarter-turn rotation, a closure cap that slides in laterally without rotating, a nut that threads onto an exterior of the connector 300, and so forth.

The second set screw 316 can include an exterior thread configured to mate with the interior threads formed on the arms 318, 320 of the body 302 to allow the second set screw to be advanced or retracted along the axis A1 with respect to the body by rotating the second set screw about the axis A1. The second set screw 316 can include a driving interface 348 configured to receive a driver for applying a rotational force to the second set screw about the axis A1. The distal surface of the second set screw 316 can be configured to contact and bear against a rod R2 disposed in the second rod-receiving 306 recess to lock the rod to the connector 300. When tightened against the rod R2, the second set screw 316 can prevent the rod from translating relative to the connector 300 along the axis A2 and/or from rotating with respect to the connector about the axis A2. While a second set screw 316 is shown, it will be appreciated that other locking elements can be used instead or addition, such as a closure cap that advances and locks by quarter-turn rotation, a closure cap that slides in laterally without rotating, a nut that threads onto an exterior of the connector 300, and so forth.

Figure 3F:
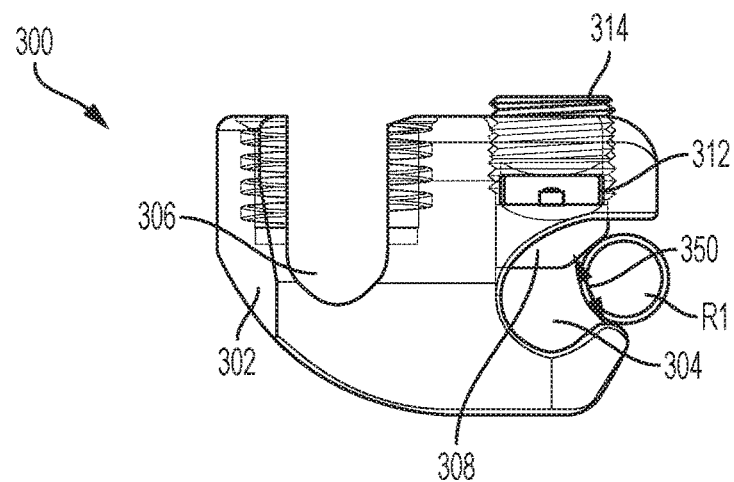
FIG. 3F is a side view of the connector of FIG. 3A in a first configuration, with a body of the connector shown as transparent.
Figure 3G:
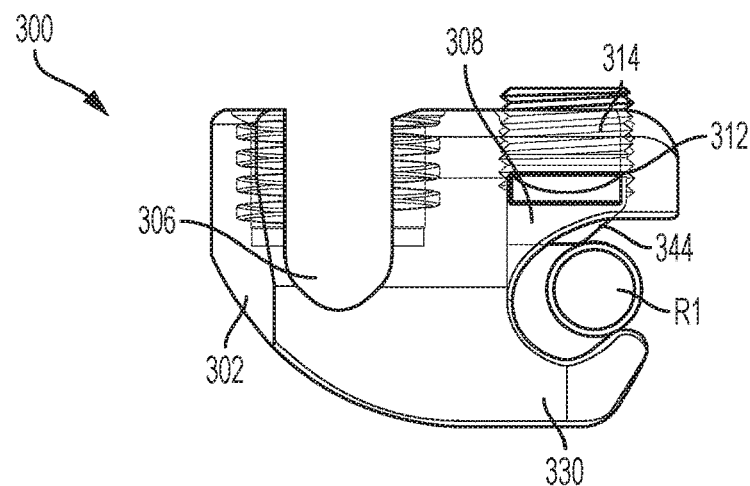
FIG. 3G is a side view of the connector of FIG. 3A in a second configuration, with a body of the connector shown as transparent.
Figure 3H:
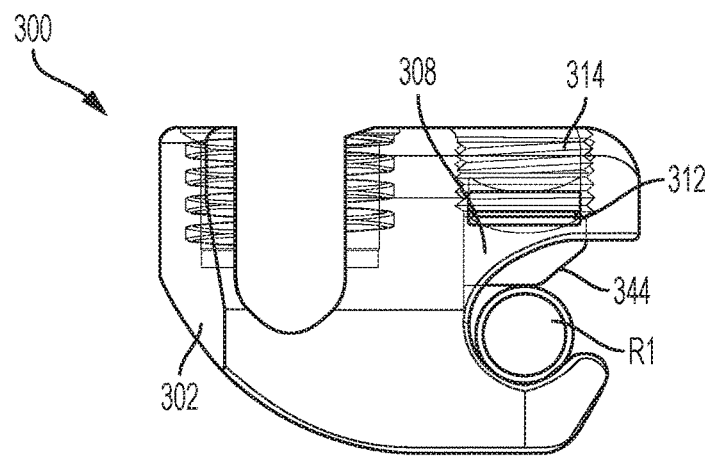
FIG. 3H is a side view of the connector of FIG. 3A in a third configuration, with a body of the connector shown as transparent.

Operation of the connector 300 is illustrated schematically in FIGS. 3F-3H.

As shown in FIG. 3F, the connector 300 can have a resting configuration in which no rod is disposed in the first or second rod-receiving recesses 304, 306. In this configuration, the biasing force of the leaf spring 312 can cause the rod pusher 308 to slide distally towards the first rod-receiving recess 304.

In the resting configuration, the wing portion 330 of the body 302 and the distal end of the rod pusher 308 can define an aperture 350 that is smaller than the diameter of a first rod R1 to which the connector 300 is to be coupled. Accordingly, as shown in FIG. 3G, as the rod R1 is inserted into the first rod-receiving recess 304, the rod bears against the rod pusher 308 to move the connector 300 out of the resting configuration. Insertion of the rod R1 can move the rod pusher 308 proximally along the axis A6, thereby compressing the leaf spring 312 within the through-bore 324. As the largest cross-sectional portion of the rod R1 is positioned in the aperture 350, the rod pusher 308 can be displaced to its furthest distance from the first rod-receiving recess 304.

As shown in FIG. 3H, once the largest cross-sectional portion of the rod R1 clears the aperture 350 as the rod is seated in the first rod-receiving recess 304, the biasing force of the leaf spring 312 can cause the rod pusher 308 to move distally, back along the axis A6 towards the first rod-receiving recess. This movement can at least partially close the aperture 350 around the rod R1 to capture the rod in the first rod-receiving recess 304. The biasing force of the leaf spring 312 can resist retrograde movement of the rod pusher 308 and thus resist disconnection of the connector 300 from the first rod R1. The leaf spring 312 can be at least partially compressed when the rod R1 is fully seated in the recess 304, such that the rod pusher 308 exerts a continuous drag force on the rod R1. When the connector 300 is positioned as desired with respect to the first rod R1, the first set screw 314 can be tightened to lock the rod in the first rod-receiving recess 304. As the first set screw 314 is tightened, the rod pusher 308 can be pressed distally, firmly into contact with the rod R1. When the first set screw 314 is tightened, the connector 300 can be locked to the first rod R1 to resist or prevent translation of the rod R1 with respect to the connector along the axis A4 and to resist or prevent rotation of the rod R1 with respect to the connector about the axis A4. A second rod R2 can be positioned in the second rod-receiving recess 306 and the second set screw 316 can be tightened to lock the rod R2 to the body 302.

The connector 300 can thus be used to connect a first spinal rod R1 to a second spinal rod R2. While use of the connector 300 with first and second spinal rods is generally described herein, it will be appreciated that the connector can instead be configured for use with other types of orthopedic hardware, whether implanted or external. For example, one or both halves of the connector 300 can be modified to couple other various components to each other (e.g., to couple a rod to a plate, to couple a plate to a plate, to couple a rod to cable, to couple a cable to a cable, and so forth). By way of further example, half of the connector 300, e.g., the portion of the body in which the second rod-receiving recess 306 is formed, can be replaced with an integral rod, a transverse bar, a cable connector, a plate with an opening formed therein for receiving a bone anchor, and so forth. In some embodiments, the structure of the connector 300 for attaching the second rod R2 can be a mirror image of the opposite half of the connector 300. In other words, the connector 300 can include two leaf springs 312, two rod pushers 308, etc.

The connector 300 can provide various benefits for the user and/or patient. For example, the biased rod pusher 308 can provide tactile feedback when the connector 300 is "snapped" onto the first rod R1, giving the user confidence that the rod has been attached successfully before tightening the connector. The biased rod pusher 308 can also apply friction or "drag" to the rod R1 prior to locking the set screw 314, helping to keep the connector 300 in place and prevent "flopping" while still allowing free movement when intended by the user. The snap and drag features of the connector 300 can be completely independent of the set screw 314, such that the connector can snap and drag onto a rod R1 regardless of whether the set screw 314 is tightened or even present in the connector. By way of further example, the low-profile geometry of the wing portion 330 of the connector 300 can allow the connector to be used in surgical areas where space is limited (e.g., in the cervical area of the spine). In an exemplary method, the wing portion 330 of the connector 300 can be hooked onto a first rod R1 at a location between two bone anchors to which the rod is coupled, the two bone anchors being implanted in adjacent vertebral levels of the cervical spine. As yet another example, the connector 300 can facilitate independent locking of the first and second rods R1, R2. This can allow the connector 300 to be locked to the first rod R1 to limit or prevent movement of the connector before the second rod R2 is attached and/or locked.

FIGS. 4A-4K illustrate an exemplary embodiment of a connector 400. Except as indicated below and as will be readily appreciated by one having ordinary skill in the art, the structure and operation of the connector 400 is substantially similar to that of the connector 300, and therefore a detailed description is omitted here for the sake of brevity.

As shown, the connector 400 can include a body 402 that defines first and second rod-receiving recesses 404, 406, a rod pusher 408, a bias element or spring wire 412, a first locking element or set screw 414, and a second locking element or set screw 416. The rod pusher 408 can be biased by the spring wire 412 in a direction that urges the rod pusher into a first rod R1 disposed in the first rod-receiving recess 404. The first set screw 414 can be tightened to lock the connector 400 to the first rod R1. The second set screw 416 can be tightened to lock a second rod R2 in the second rod-receiving recess 406 of the connector 400. The illustrated connector 400 can thus allow for independent locking of first and second rods R1, R2 to the connector. The connector 400 can include one or more low-profile portions to facilitate use in tight spaces. For example, the first rod-receiving recess 404 can be formed in a portion 430 of the connector body 402 having a reduced-profile, e.g., to fit between bone anchors implanted in adjacent levels of the cervical spine.

The body 402 can include proximal and distal ends 402p, 402d that define a proximal-distal axis A1. The proximal end 402p of the body 402 can include a pair of spaced apart arms 418, 420 that define the second rod-receiving recess 406 therebetween. A rod R2 disposed in the second rod-receiving recess 406 can have a central longitudinal rod axis A2.

Figure 4A:
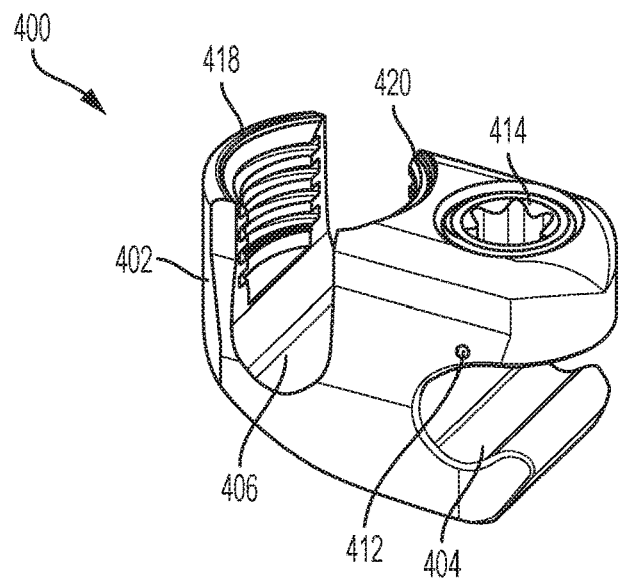
FIG. 4A is a perspective view of a connector.
Figure 4B:
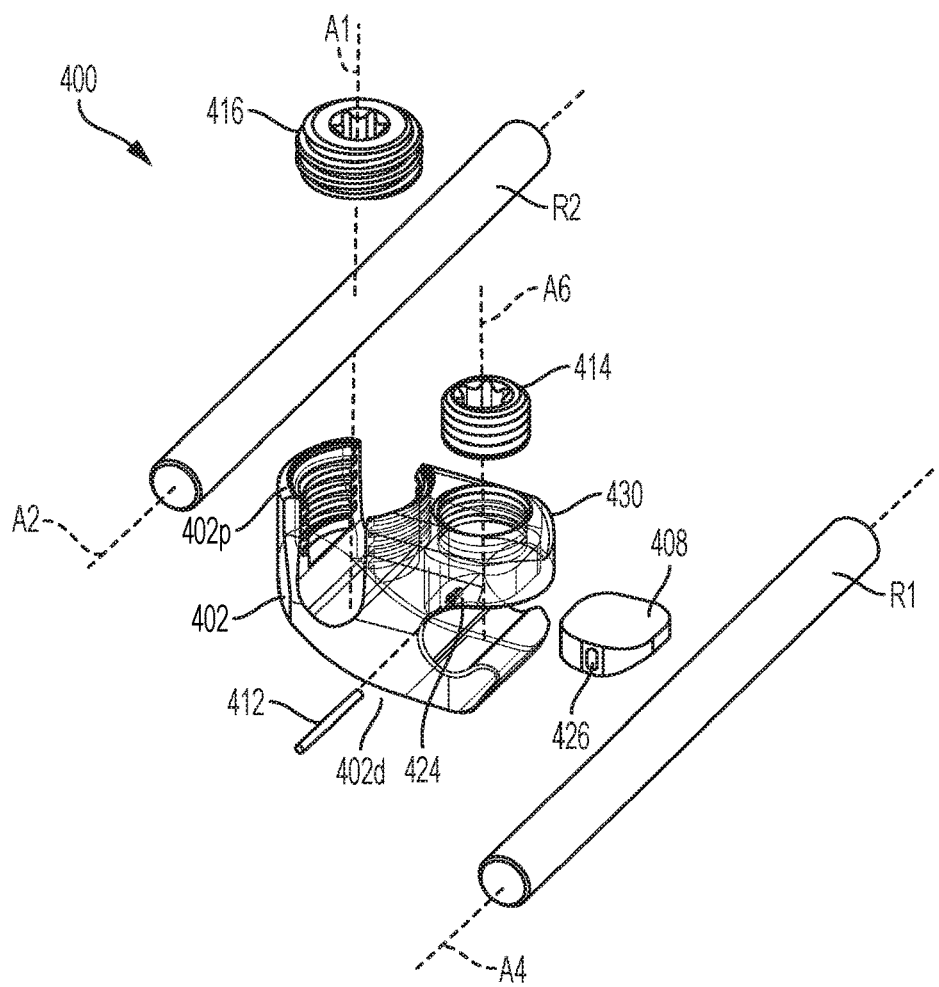
FIG. 4B is an exploded perspective view of the connector of FIG. 4A shown with first and second spinal rods, with a body of the connector shown as transparent.
Figure 4C:
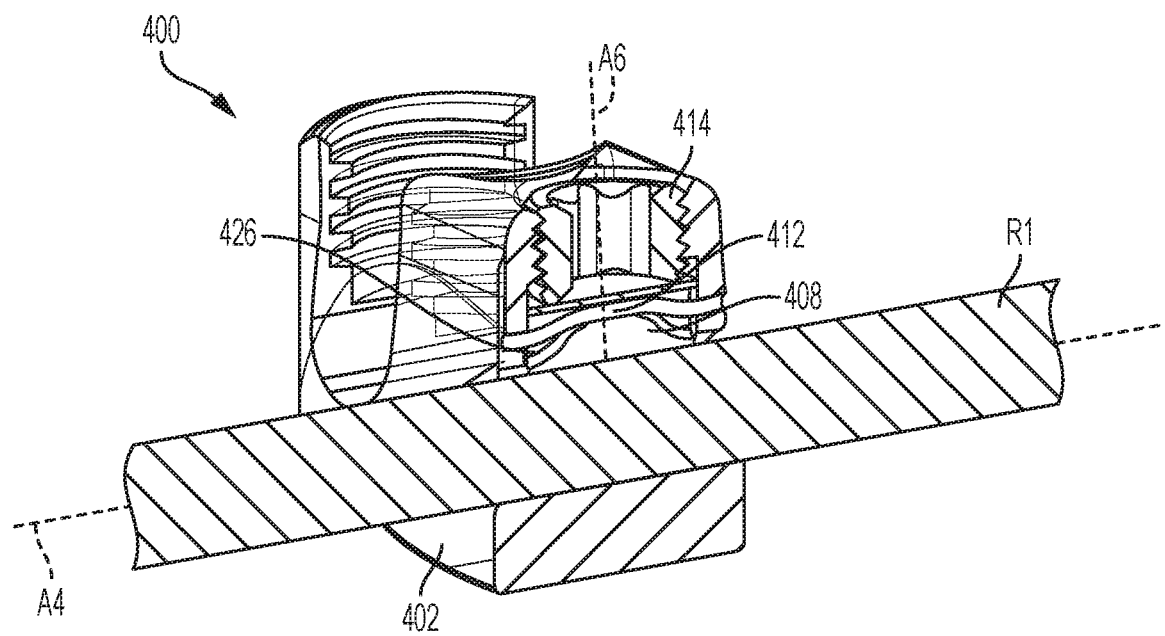
FIG. 4C is a sectional perspective view of the connector of FIG. 4A having a spring wire oriented in a first direction, with a body of the connector shown as transparent.
Figure 4D:
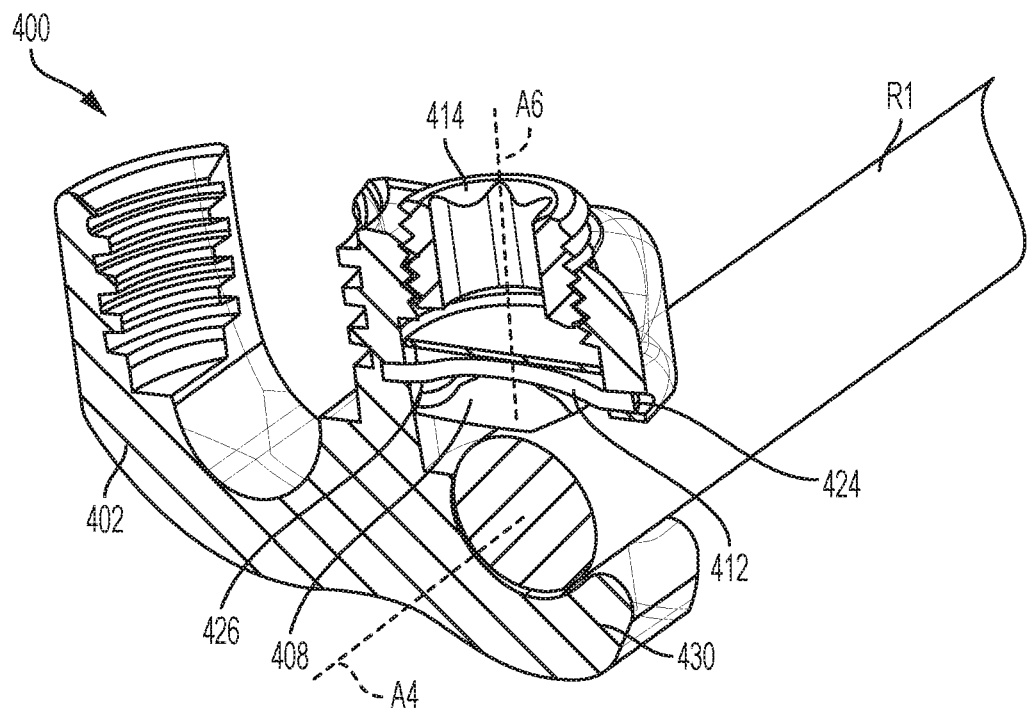
FIG. 4D is a sectional perspective view of the connector of FIG. 4A having a spring wire oriented in a second direction, with a body of the connector shown as transparent.
Figure 4E:
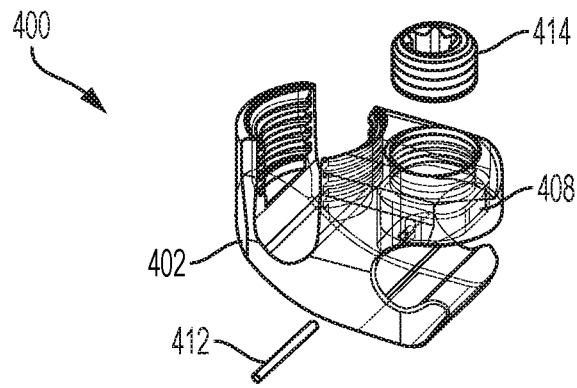
FIG. 4E is a perspective view of the connector of FIG. 4A in a first state of assembly, with a body of the connector shown as transparent.
Figure 4F:
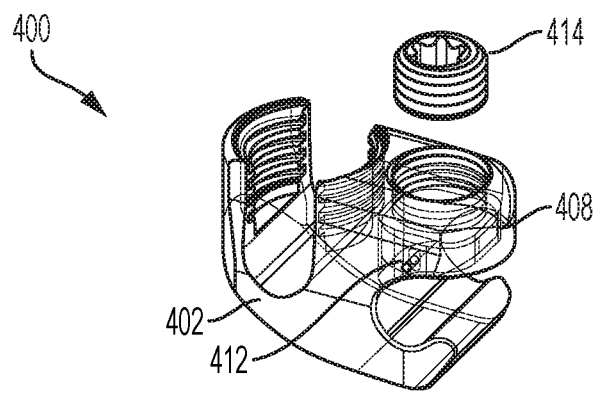
FIG. 4F is a perspective view of the connector of FIG. 4A in a second state of assembly, with a body of the connector shown as transparent.
Figure 4G:
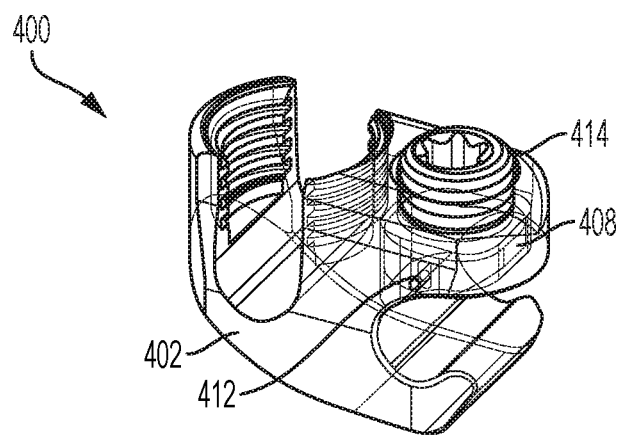
FIG. 4G is a perspective view of the connector of FIG. 4A in a third state of assembly, with a body of the connector shown as transparent.

As shown for example in FIG. 4C, a spring wire 412 can be used to bias the rod pusher 408 towards the first rod-receiving recess 404, instead of or in addition to the leaf spring 312 of the connector 300. The rod pusher 408 can include a through bore 426 sized to receive the spring wire 412 therein. In at least some positions of the rod pusher 408 with respect to the body 402, the through-bore 426 of the rod pusher can be aligned with the through-bore 424 of the body, such that the spring wire 412 extends through both through-bores 424, 426. The through-bore 426 can include a middle portion and opposed end portions. The middle portion of the through-bore 426 can approximate the dimensions of the spring wire 412. For example, the middle portion can be cylindrical and can have a diameter that is substantially equal to the diameter of the spring wire 412. The end portions of the through-bore 426 can be elongated or can otherwise have a dimension greater than the diameter of the spring wire 412 to allow the rod pusher 408 to translate along the tunnel axis A6 and to accommodate the bend radius of the spring wire 412 during such translation. The longitudinal axes of the through-bores 424, 426 and the spring wire 412 can extend perpendicular or substantially perpendicular to the axis A6 and parallel or substantially parallel to the axis A4, as shown in FIG. 4C. Alternatively, as shown in FIG. 4D, the longitudinal axes of the through-bores 424, 426 and the spring wire 412 can extend perpendicular or substantially perpendicular to the axis A6 and perpendicular or substantially perpendicular to the axis A4.

Figure 4H:
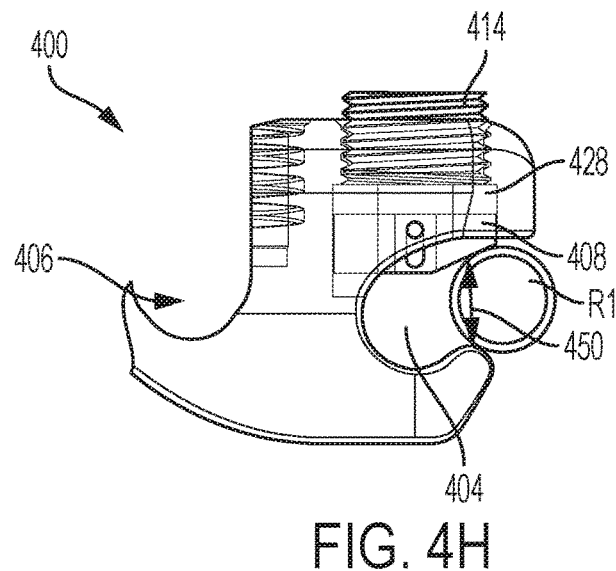
FIG. 4H is a side view of the connector of FIG. 4A in a first configuration, with a body of the connector shown as transparent.
Figure 4I:
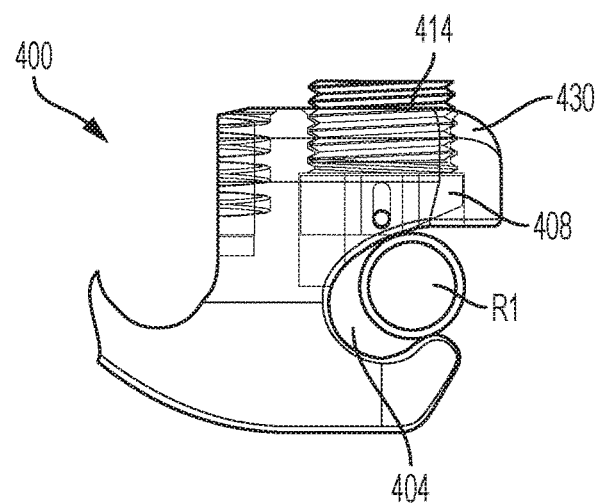
FIG. 4I is a side view of the connector of FIG. 4A in a second configuration, with a body of the connector shown as transparent.
Figure 4J:
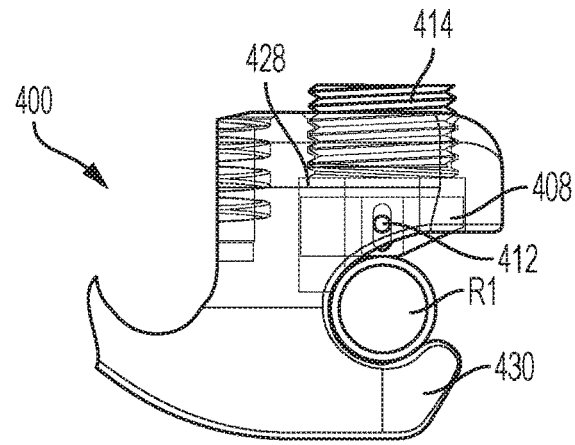
FIG. 4J is a side view of the connector of FIG. 4A in a third configuration, with a body of the connector shown as transparent.

As shown in FIGS. 4H-4J, the rod pusher 408 can be configured to translate along the axis A6 within a tunnel 428 formed in the body 402. The rod pusher 408 can translate within the tunnel 428 under the bias of the spring wire 412 to provide a snap and drag feature with respect to the first rod R1.

Figure 4K:
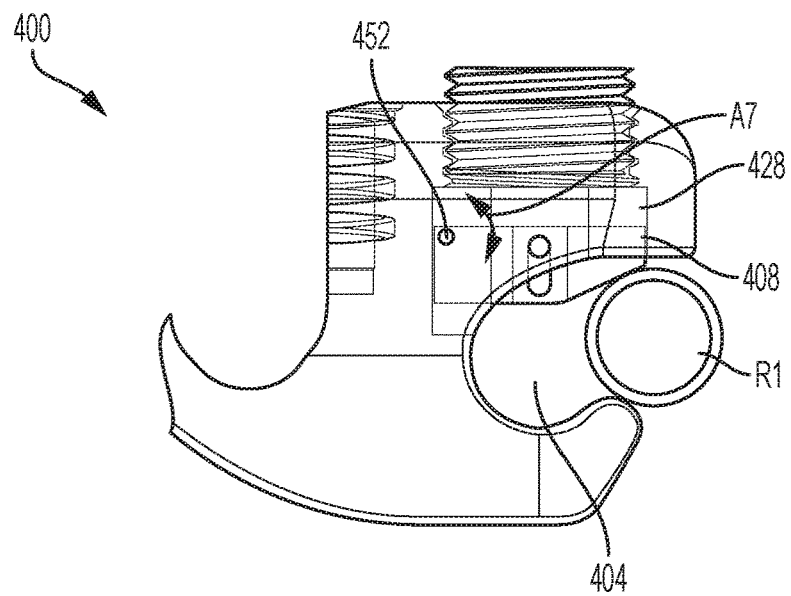
FIG. 4K is a side view of the connector of FIG. 4A having a pivoting rod pusher, with a body of the connector shown as transparent.

In other embodiments, the rod pusher 408 can pivot with respect to the body 402 about a rotation axis instead of or in addition to translating. For example, as shown in FIG. 4K, the rod pusher 408 can be pivotally mounted within the tunnel 428 on a pivot pin or axle 452. The rod pusher 408 can therefore rotate along the arc A7 as a rod R1 is inserted into the first rod-receiving recess 404. Apart from this pivoting movement, operation of the connector 400 shown in FIG. 4K is the same as described above.

An exemplary method of using the connectors disclosed herein is described below.

Figure 5:
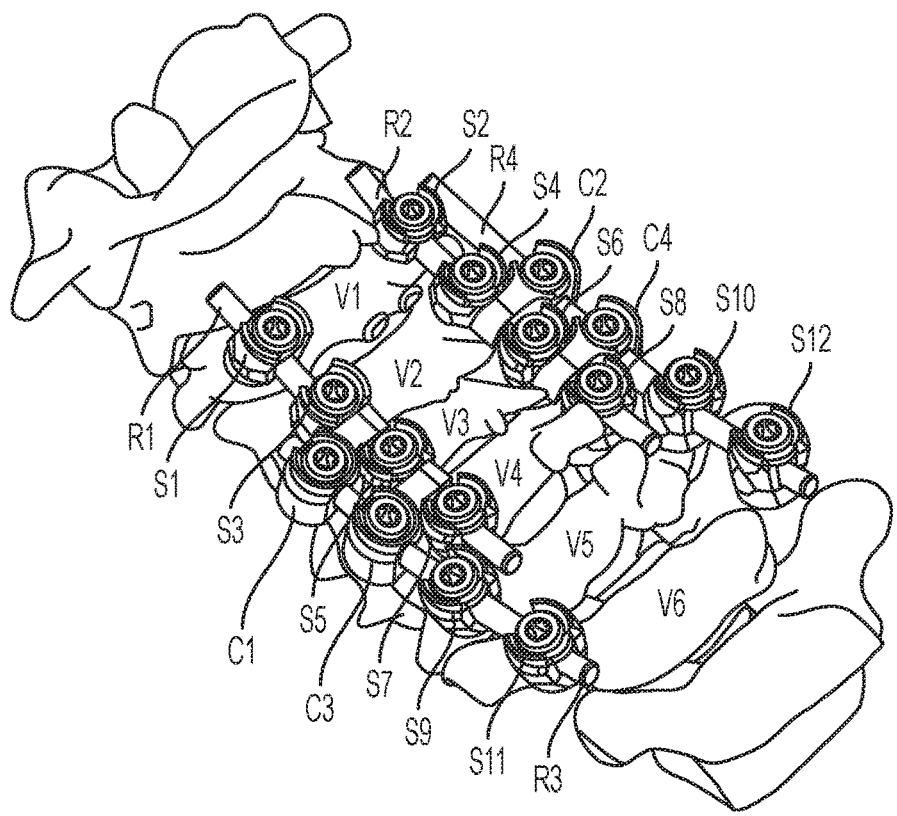
FIG. 5 is a perspective view of a human spine with a fixation system attached thereto.

The procedure can begin by forming an open or percutaneous incision in the patient to access a target site. The target site can be one or more vertebrae, a long bone or multiple portions of a long bone, or any other bone or non-bone structure of the patient. As shown in FIG. 5, the target site can be multiple vertebrae in the patient's cervical and thoracic spine.

Bone anchors can be driven into one or more of the vertebrae and spinal rods can be attached thereto using known techniques. In the illustrated example, bilateral spinal rods R1, R2 are coupled to four adjacent vertebrae V1-V4 using eight bone anchors S1-S8. In addition, bilateral rods R3, R4 are coupled to the next two adjacent vertebrae V5-V6 using four bone anchors S9-S12. The rods R1, R2 can be connected to the rods R3, R4, respectively, using four connectors C1-C4 of the type described herein (e.g., any of the connectors 100, 200, 300, 400 or combinations or variations thereof).

As shown, the low-profile nature of the connectors C1-C4 can allow them to be installed at adjacent vertebral levels on the same rod (e.g., between V2/V3 and between V3/V4). As also shown, the connectors C1-C4 can connect to the rods R1, R2 between bone anchors installed in adjacent vertebral levels.

The connectors C1-C4 can "snap" onto the rods R1, R2, thereby providing tactile feedback to the user that the connectors are secured.

The connectors C1-C4 can "drag" against the rods R1, R2, thereby allowing for provisional positioning and retention of the connectors prior to locking the connectors to the rods R1, R2 and/or to the rods R3, R4.

The snap and/or drag features of the connector C1-C4 can provide confidence that the connector will stay in position, can make construct assembly easier, and can reduce the risk of having to retrieve dropped connectors from vital vascular or neural structures.

The connectors C1-C4 can include independent locking features such that they can be locked to the rods R1, R2 prior to being locked to the rods R3, R4 or vice versa.

The connectors C1-C4 can include single-step locking features such that they can be simultaneously locked to their respective rods. For example, connector C1 can be simultaneously locked to rods R1 and R3.

All of the rods R1-R4, the connectors C1-C4, and the bone anchors S1-S12 can be installed in a single procedure.

Alternatively, the rods R1, R2 and the bone anchors S1-S8 may have been installed in a previous procedure, and the current procedure can be a revision procedure in which the rods R3, R4, the connectors C1-C4, and the bone anchors S9-S12 are installed to extend the previously-installed construct to additional levels.

The connectors C1-C4 can be attached to position the rods R1-R4 such that they are substantially parallel to one another and substantially lie in a common coronal plane as shown. The connectors C1-C4 can also be rotated 90 degrees from the orientation shown to position the rod pairs R1, R3 and R2, R4 such that they substantially lie in respective common sagittal planes.

The above steps can be repeated to install additional rods and/or connectors at the same or at different vertebral levels. Final tightening or other adjustment of the construct can be performed and the procedure can be completed using known techniques and the incision closed.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

While the methods illustrated and described herein generally involve attaching spinal rods to multiple vertebrae, it will be appreciated that the connectors and methods herein can be used with various other types of fixation or stabilization hardware, in any bone, in non-bone tissue, or in non-living or non-tissue objects. The connectors disclosed herein can be fully implanted, or can be used as part of an external fixation or stabilization system. The devices and methods disclosed herein can be used in minimally-invasive surgery and/or open surgery.

The devices disclosed herein and the various component parts thereof can be constructed from any of a variety of known materials. Exemplary materials include those which are suitable for use in surgical applications, including metals such as stainless steel, titanium, or alloys thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described.

The invention claimed is:

1. A connector, comprising:
   a body that defines a first rod-receiving recess having an aperture for receiving a first rod therein and a second rod-receiving recess having an aperture for receiving a second rod therein, the body having proximal and distal ends that define a proximal-distal axis extending therebetween;

a rod pusher configured to move within a tunnel of the body in a direction that is substantially perpendicular to the proximal-distal axis, the rod pusher having a through-bore formed therein;

a bias element configured to be received in one or more of the body and the through-bore transversely to the proximal-distal axis, the bias element being configured to exert a biasing force onto the rod pusher toward the first rod-receiving recess to at least partially reduce a size of the aperture of the first rod-receiving recess to capture the first rod therein.

2. The connector of claim 1, wherein the aperture of the first rod-receiving recess faces in an opposite direction of the aperture of the second rod-receiving recess.

3. The connector of claim 2, wherein the aperture of the first rod-receiving recess is distal-facing and the aperture of the second rod-receiving recess is proximal-facing.

4. The connector of claim 1, wherein the bias element extends through opposing walls of one or more of the body and the through-bore.

5. The connector of claim 1, further comprising a set screw threadably received in one of the first or second rod-receiving recesses in the body to further capture the first rod within the first rod-receiving recess and to capture the second rod within the second rod-receiving recess.

6. The connector of claim 5, wherein the set screw is received in the second rod-receiving recess.

7. The connector of claim 6, wherein the second rod is disposed between the set screw and the rod pusher.

8. The connector of claim 5, wherein the second rod is disposed between the second-rod receiving recess and the set screw.

9. The connector of claim 1, wherein the rod pusher bears against the first and second rods simultaneously.

10. The connector of claim 1, wherein the bias element exerts the biasing force onto the rod pusher in its resting state.

11. The connector of claim 1, wherein the bias element is deformed from its resting state when the first rod is captured within the first rod-receiving recess to press the rod pusher against the first rod.

12. The connector of claim 1, wherein the tunnel extends between the first rod-receiving recess and the second rod-receiving recess, such that movement of the rod pusher alternatively increases or decreases the size of the apertures of the first rod-receiving recess and the second rod-receiving recess.

13. The connector of claim 1, wherein the through-bore in the rod pusher includes a cylindrical middle portion and opposed end portions that are elongated in the direction of the rod pusher axis.

14. The connector of claim 1, further comprising a saddle disposed in a cavity formed in the body.

15. The connector of claim 14, wherein at least a portion of the cavity is formed by the second rod-receiving recess.

16. The connector of claim 14, wherein the saddle is translatable along the proximal-distal axis of the body.

17. The connector of claim 14, wherein the saddle includes a ramped bearing surface configured to contact and bear against the rod pusher.

18. The connector of claim 1, wherein the rod pusher is unitary.

19. A method of connecting spinal rods, comprising:

passing a first spinal rod into a first rod-receiving recess formed in a body portion of a connector having the first rod-receiving recess and a second rod-receiving recess such that the first spinal rod exerts a force onto a rod pusher disposed within the first and second rod-receiving recesses to displace the rod pusher further into the second rod-receiving recess;

passing a second spinal rod into the second rod-receiving recess defined by a pair of spaced apart arms such that the second spinal rod bears against the rod pusher to displace the rod pusher further into the first rod-receiving recess and to prevent movement of the rod pusher toward the second rod-receiving recess; and tightening a set screw within the body by passing the set screw along the pair of spaced apart arms to lock the second rod within the second rod-receiving recess and to lock the first rod within the first rod-receiving recess.

20. The method of claim 19, wherein the set screw is disposed within the second rod-receiving recess.

21. The method of claim 19, wherein passing the first spinal rod into the first rod-receiving recess counters a biasing force exerted onto the rod pusher by a spring member disposed within the rod pusher and deforms the spring member to allow displacement of the rod pusher toward the second rod-receiving recess.

22. The method of claim 21, wherein, after the first spinal rod is disposed within the first rod-receiving recess, the biasing force displaces the rod pusher toward the first rod-receiving recess to capture the first rod within the first rod-receiving recess.

23. The method of claim 21, wherein the spring member is disposed within the rod pusher along an axis that is substantially perpendicular to an axis of the displacement of the rod pusher.

24. The method of claim 19, wherein the set screw is in contact with the second spinal rod when the second spinal rod is locked within the second rod-receiving recess and the first spinal rod is locked within the first rod-receiving recess.

* * * * *